United States Patent
Schulman et al.

(10) Patent No.: US 7,515,012 B2
(45) Date of Patent: *Apr. 7, 2009

(54) SYSTEM AND METHOD FOR AUTOMATIC TUNING OF A MAGNETIC FIELD GENERATOR

(75) Inventors: Joseph H. Schulman, Santa Clarita, CA (US); Dale A. Lewis, Pine Mountain, CA (US); Donald J. Hancock, Thousand Oaks, CA (US); Martin J. Vogel, Valencia, CA (US); Adam Vogel, legal representative, Valencia, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 276 days.

This patent is subject to a terminal disclaimer.

(21) Appl. No.: 11/360,307

(22) Filed: Feb. 22, 2006

(65) Prior Publication Data

US 2006/0192628 A1    Aug. 31, 2006

Related U.S. Application Data

(63) Continuation-in-part of application No. 10/429,427, filed on May 5, 2003, now Pat. No. 7,015,769.

(60) Provisional application No. 60/661,760, filed on Mar. 14, 2005.

(51) Int. Cl.
*H03G 11/04* (2006.01)
*A61N 2/02* (2006.01)
*A61N 1/08* (2006.01)

(52) U.S. Cl. .................. 333/17.1; 607/2; 607/60; 607/65; 607/155

(58) Field of Classification Search ............. 333/17.1, 333/174, 180; 607/2, 60, 61, 65, 155; 336/10, 336/87, 150
See application file for complete search history.

(56) References Cited

U.S. PATENT DOCUMENTS 3,614,665 A    10/1971    Carroll et al.

(Continued)

FOREIGN PATENT DOCUMENTS

EP    551813    7/1993

(Continued)

*Primary Examiner*—Barbara Summons
(74) *Attorney, Agent, or Firm*—Malcolm J. Romano

(57) ABSTRACT

An automatic tuning system for a magnetic field generating tuned circuit includes a processor configured to maintain the resonant frequency of a tuned circuit equal to a reference frequency. The tuned circuit is driven by a power amplifier whose output provides an amplified signal at the reference frequency. The tuned circuit includes a magnetic field generating inductor and a bank of individually switchable capacitors controlled by the processor capable of adding and removing the respective capacitances to and from the tuned circuit. The inductor includes a Faraday shield to shield the tuned circuit from the influence of electric fields. In an embodiment of the invention, the variable capacitor is in the form of a diode variable capacitor (varicap) in parallel circuit relationship with the tuned circuit capacitor and the inductor. In an alternate embodiment the inductor and a fixed capacitor are in series circuit relationship with the varicap in parallel circuit relationship with the fixed capacitor and the tuning sequence relies on a phase locked loop using the phase of a reference frequency signal and the phase of the inductor voltage as control parameters.

15 Claims, 20 Drawing Sheets

U.S. PATENT DOCUMENTS

| | | | | |
|---|---|---|---|---|
| 4,210,152 | A * | 7/1980 | Berry | 607/98 |
| 4,793,356 | A | 12/1988 | Misic et al. | |
| 5,350,413 | A * | 9/1994 | Miller | 607/61 |
| 5,644,598 | A * | 7/1997 | Bidese | 375/258 |
| 6,023,166 | A | 2/2000 | Eydelman et al. | |
| 6,070,803 | A * | 6/2000 | Stobbe | 235/492 |
| 6,212,431 | B1 * | 4/2001 | Hahn et al. | 607/61 |
| 6,349,116 | B1 * | 2/2002 | Hash et al. | 375/258 |
| 6,591,139 | B2 * | 7/2003 | Loftin et al. | 607/60 |
| 6,889,036 | B2 * | 5/2005 | Ballweber et al. | 455/292 |
| 7,015,769 | B2 * | 3/2006 | Schulman et al. | 333/17.1 |
| 7,062,331 | B2 * | 6/2006 | Zarinetchi et al. | 607/61 |
| 7,190,153 | B2 * | 3/2007 | Stover et al. | 323/282 |
| 2003/0083836 | A1 * | 5/2003 | Spencer | 702/107 |
| 2003/0206065 | A1 * | 11/2003 | Gomez | 331/16 |

FOREIGN PATENT DOCUMENTS

| | | |
|---|---|---|
| EP | 1374948 | 1/2004 |
| EP | 1383234 | 1/2004 |
| JP | 01 236043 | 9/1989 |

\* cited by examiner

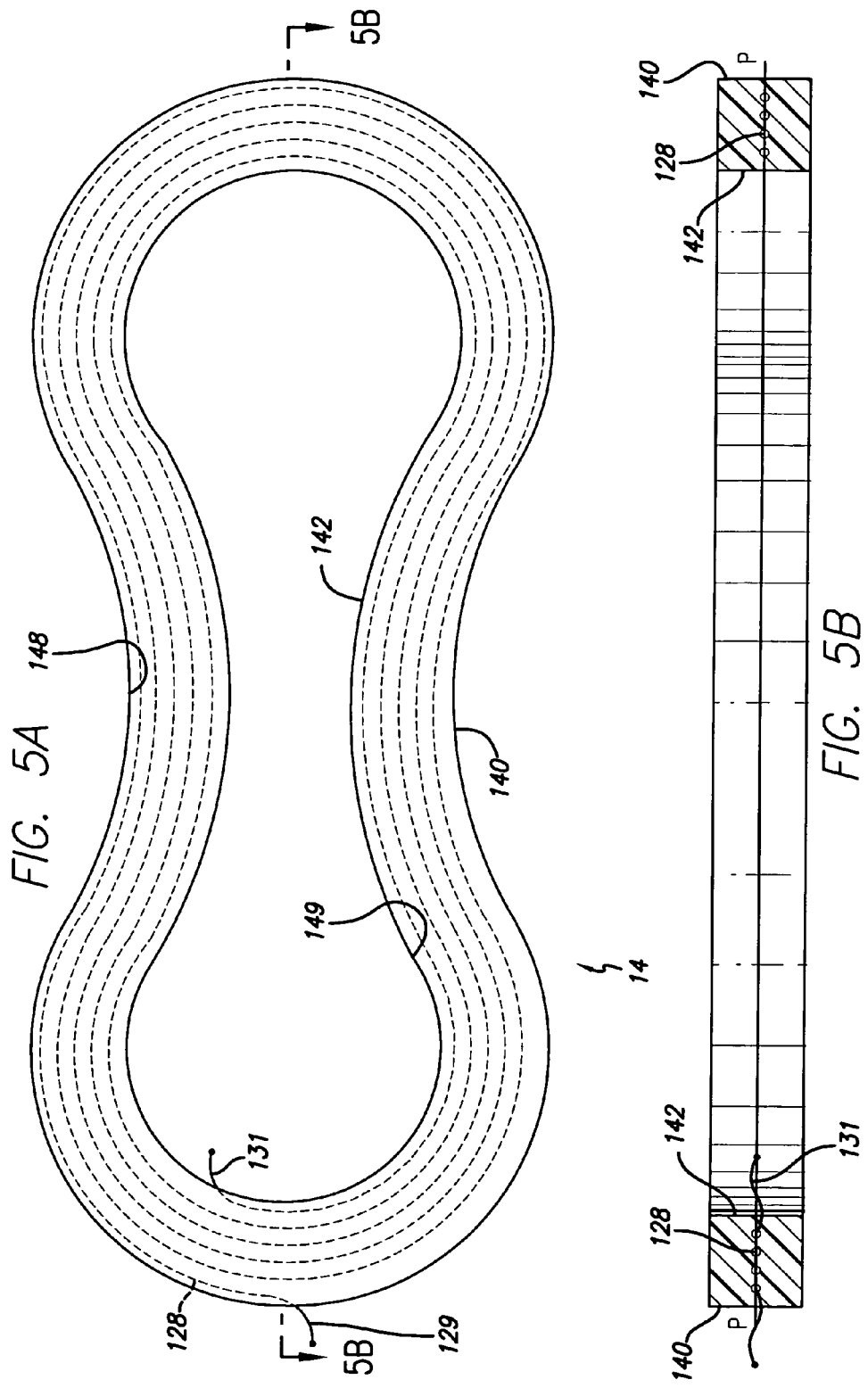

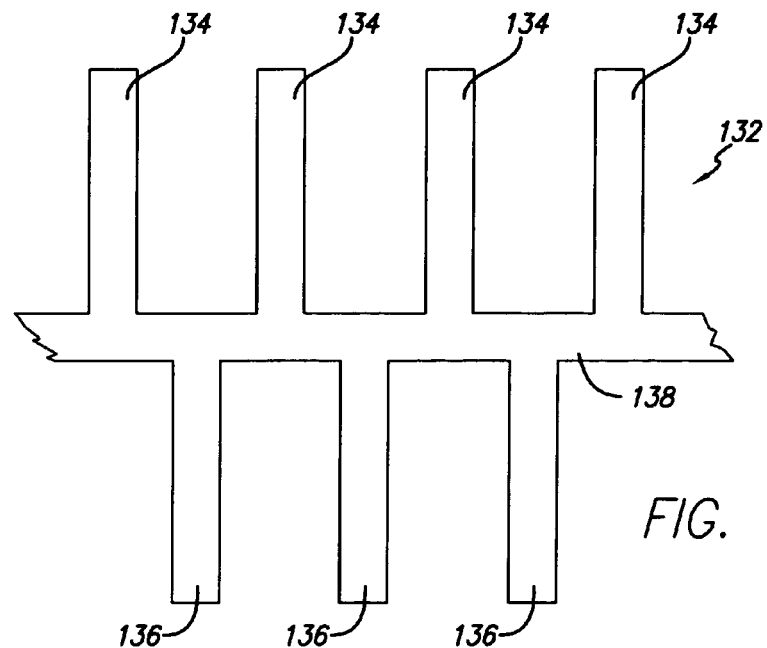
FIG. 6A
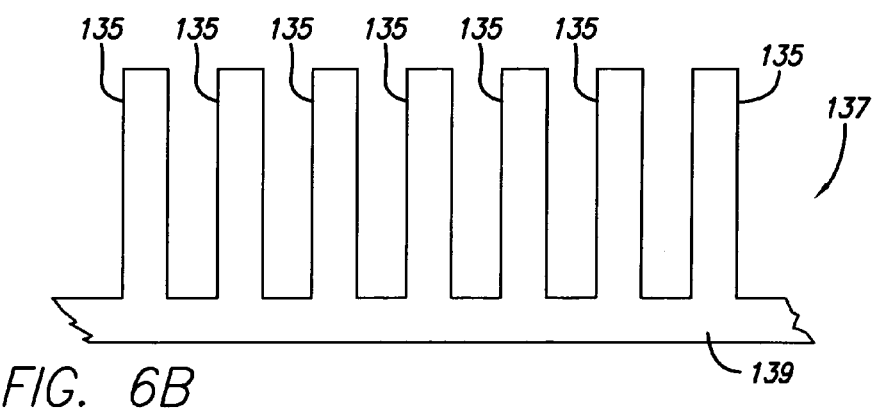
FIG. 6B
FIG. 7
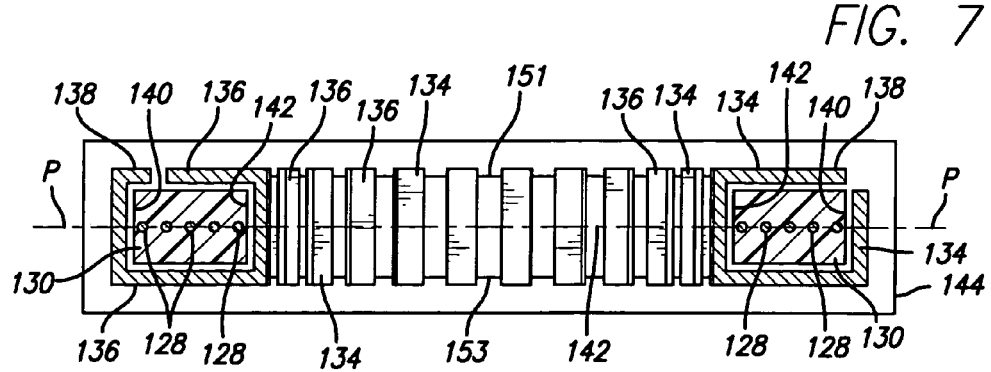

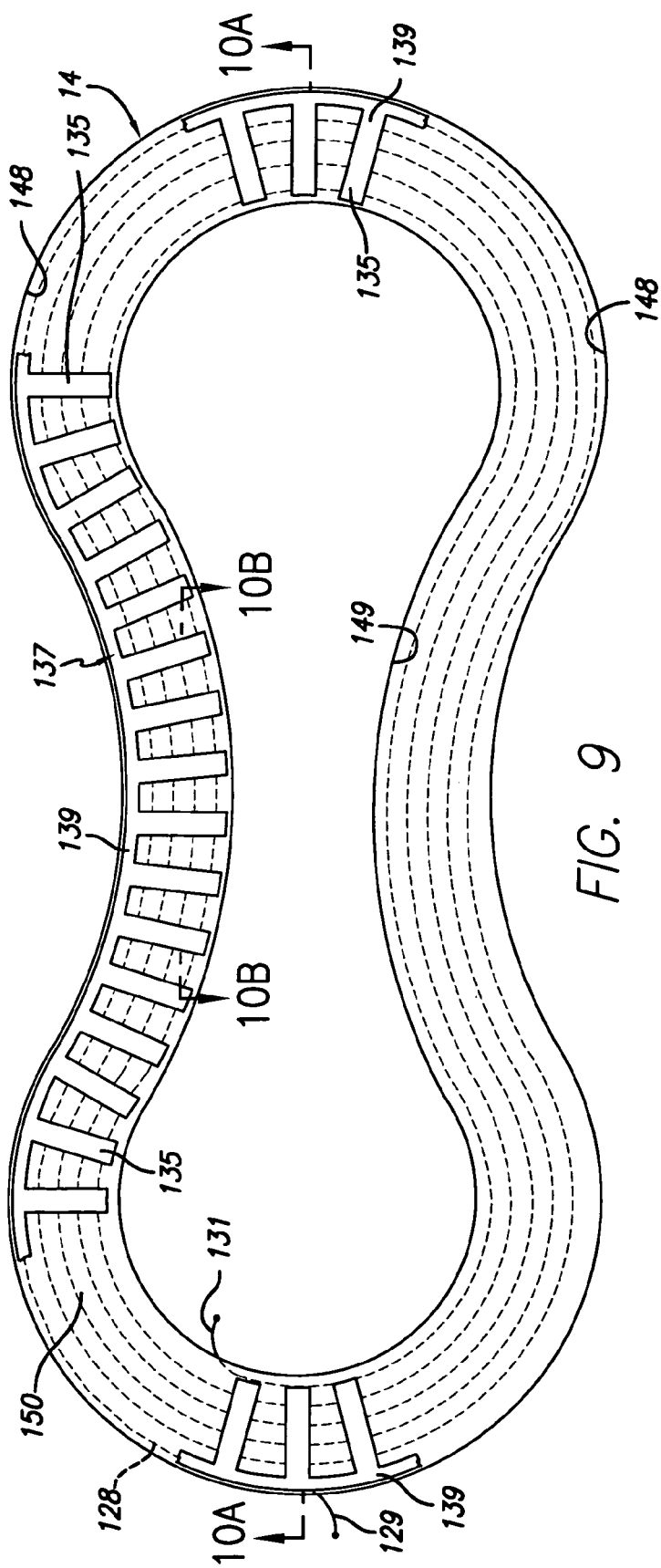
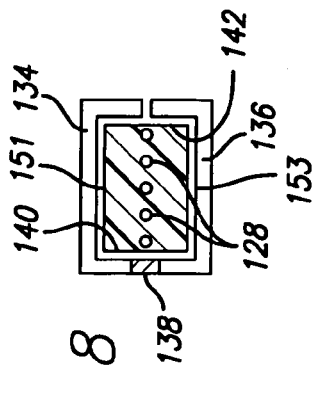
FIG. 9
FIG. 8

SYSTEM AND METHOD FOR AUTOMATIC TUNING OF A MAGNETIC FIELD GENERATOR

CROSS REFERENCE TO RELATED APPLICATION

This application is a continuation-in-part of U.S. non-provisional application Ser. No. 10/429,427 filed May 5, 2003, which issued on Mar. 21, 2006 as U.S. Pat. No. 7,015,769. This application also claims the benefit of U.S. provisional application No. 60/661,760 filed Mar. 14, 2005.

FIELD OF THE INVENTION

The present invention relates to a system and method for tuning a magnetic field generator, more particularly, to a system and method that automatically provides efficient power transfer from a power source to a tuned circuit having a magnetic field generating inductor.

BACKGROUND OF THE INVENTION

Implantable medical devices for remedial treatment of and compensation for cardiac, neural and muscular disorders, are known in the art. These devices range from cardiac pacemakers as described in U. S. Pat. No. 4,712,555 to Thornander et al., to microstimulators as described in U. S. Pat. No. 6,208,894 to Schulman et al. The quest for minimization of such devices, especially in the area of microdevices such as microstimulators and microsensors, has presented the challenge of efficiently providing a reliable and stable power source to power the device or charge its internal battery as well as a communication medium to facilitate information, data and command signal transfer and exchange between the microdevice and a corresponding microdevice control unit. Heretofore, wireless communication between the control unit and the implanted device including microdevices, has been described as being implemented by means of a modulated sound signal, time varying (such as an alternating current AC) magnetic field or light source. In certain instances, wireless communication, which is also intended as a means of power delivery to an implanted microdevice, is by way of a time varying magnetic field generated by an inductor positioned in proximity to the microdevice. The inductor may be formed on a flexible support which contains a series of closely wound electrically conductive wires that when energized, generate a magnetic field in the vicinity of such wires. Utility is found in the use of such flexible support when it is desired to bring the inductor in close proximity with microdevices that are implanted in regions of the body characterized as being very contoured. For example, in the instance when microdevices are implanted on either side of a patient's neck, the inductor and therefore the inductor support must be sufficiently flexible and pliable to permit wrapping the inductor around the patient's neck so that the inductor will simultaneously be in proximity with all the implanted microdevices in the neck. The net result of the inductor being so positioned, is that maximum magnetic coupling is theoretically achieved between the inductor and microdevice, so that communication whether it is intended for example, for data transfer or charging a rechargeable microdevice battery, will be most efficiently and reliably realized. Data transmission between such devices may involve the use of magnetic field modulation techniques using known data transmission protocols.

The basis for good wireless communication in cases where magnetic field coupling is the technique of choice, is that the magnetic field strength should be unaffected by manipulation of the inductor support as well as the introduction of magnetic field altering implements in the vicinity of the inductor. In such cases the effective inductance value of the inductor is observed to change. This can occur if the inductor is bent or distorted when applied to fit the contour of a desired location of a body. In systems that use a power amplifier driven tuned circuit comprising an inductor and capacitors, the maximum power delivered to the tuned circuit and therefore the maximum magnetic field strength produced by the inductor, occurs when the resonant frequency of the tuned circuit matches a reference frequency, that is applied to the power amplifier, and which usually relates to the nominal values of the capacitors and the inductor. Changes in inductance value of the inductor may have a severe impact on the resonant frequency of the tuned circuit and therefore have a correspondingly negative effect on any magnetic field generated by the inductor. The fallout from such deterioration of magnetic field strength would be the deterioration of communication integrity between the microdevice and its control unit. It has been observed that inductor shape changes from circular to a flattened oval can result in a reduction of inductance value of as much as 50%. Since such inductance value changes may be dynamic in nature, what is needed is an automatic tuning system that dynamically and adaptively adjusts the resonant frequency of the tuned circuit and maintain it equal to the reference frequency.

SUMMARY

The present invention addresses the need to provide an automatic tuning system that efficiently and adaptively maximizes the power delivered to a tuned circuit that includes a magnetic field generating inductor. In accordance with an embodiment of the invention, a microcontroller based automatic tuning system is provided that includes a power source, a tuned circuit comprising an inductor and an adjustable capacitor, a power amplifier having an input coupled to a reference frequency generator and an output configured to drive the tuned circuit. The inductance value of the inductor and the capacitance value of the variable capacitor establishes the resonant frequency of the tuned circuit which is automatically tuned such that the resonant frequency is adjusted to equal the reference frequency. Normally, when the resonant frequency of the tuned circuit equals the reference frequency, maximum power will be delivered to the tuned circuit. A sense circuit is arranged to provide a signal to the microcontroller corresponding to the power delivered by the power amplifier to the tuned circuit. The microcontroller causes the variable capacitor to be adjusted so as to maximize the power delivered to the tuned circuit. In an alternate embodiment, the phase of the reference frequency and the phase of the current flowing through the inductor are compared and maintained within a predetermined range in order to maximize the power delivered to the tuned circuit.

The adjustable capacitor includes an array of capacitors, forming a bank of capacitors, that is switchable so as to be in parallel circuit arrangement with other selected capacitors of the bank. An individual bi-state switch is associated with respective ones of the capacitors in the bank, such that in a first state, the switch causes the respective capacitor to be in parallel circuit arrangement with other selected capacitors of the bank and in a second state, the switch causes the respective capacitor to be removed from parallel circuit arrangement with other selected capacitors of the bank. In a preferred embodiment, the switch is relay driven such that energizing the relay with a voltage of a first polarity causes the switch to be in the first state and energizing the relay with a voltage of a second polarity causes the switch to be in the second state. Alternate embodiments of the switch include the use of bipolar and field effect transistors. In such case, the transistors would typically be in series circuit arrangement with the respective capacitors, with the base or gate of the transistors as the case may be, actuated ultimately by the microcontroller. Alternate embodiments of the tuned circuit include a variable inductor so that adjusting the resonant frequency of the tuned circuit may include adjusting the value of the inductance of the inductor singly or in combination with adjusting the capacitance value of the adjustable capacitor.

In a preferred embodiment, a relay controller is interposed between the relays and the microcontroller to provide control of the relay based upon the status of the power delivered by the power amplifier. In a preferred embodiment, the capacitor bank includes eight switchable capacitors arranged such that the respective capacitance value is in binary progression order. Although eight capacitors have been selected, it is to be understood that a smaller or larger number of capacitors may be selected based upon design choice and the desire to either decrease or increase the tuning sensitivity, respectively. Binary progression order, requires that the capacitance value of the capacitors in the bank, doubles in value when progressing through the bank. Accordingly, if the first capacitor in the bank has, for example, a value of 1 picofarad (pF), then the second capacitor in the bank will have a value of 2 pF and the third capacitor will have a value of 4 pF and so on through the bank to the last capacitor in the bank, which for the described eight capacitor case, will have a value of 128 pF. Other capacitance value sequences are also contemplated by the present invention, as well as a continuously variable capacitor being motor driven in either a continuous or stepped fashion. In addition to the capacitor bank, two additional capacitors are included in the tuned circuit, a fixed capacitor and a trim capacitor. The resonant frequency of the tuned circuit is established based upon the capacitance value and the inductor value of the respective elements. The maximum power delivered to the tuned circuit occurs when the resonant frequency of the tuned circuit equals that of the reference frequency. The fixed capacitor and trim capacitor are selected to establish a resonant frequency somewhat different from that expected for an inductor having a nominal value. Accordingly, the switchable capacitors are intended to be added to the tuned circuit so as to establish a resonant frequency of the tuned circuit and thus provide the capability to add and subtract capacitance in the process of later optimizing the tuned circuit when inductance values change.

In practice, the microcontroller initially causes the first capacitor switch to be in a first state and thereby connect the first capacitor to be in parallel connection with the fixed and trim capacitors while all the other switches to be in a second state such that all but the first or smallest value capacitance of the switchable capacitors, are removed from parallel circuit connection with any other capacitor of the bank. The microcontroller detects and stores the present value of the power delivered to the tuned circuit and the capacitor switch setting giving rise to such delivered power. The microcontroller then commands that the first capacitor be placed in the second state or switched out of parallel connection and that the second capacitor in the bank be switched so as to be in parallel with the fixed and trim capacitors. A measurement of the power delivered to the tuned circuit is made and the capacitor switch setting giving rise to such delivered power is stored. The microcontroller then causes the first capacitor switch to be in the first state thereby adding the first capacitor in parallel connection with the second capacitor and the fixed and trim capacitors. A measurement of power delivered is made and the capacitor switch setting giving rise to such delivered power, is stored. The power measurement and storage of such power measurement and corresponding switch setting are repeated until every possible switch combination has been tested. Upon completion of the above protocol, the microcontroller selects the capacitor switch setting that provides the maximum power delivered for the nominal setting. By proceeding through all switch combinations, the circumstance where, for example, a double peaked maximum occurs, will be identified.

A number of capacitor switching protocols are contemplated by the present invention. By way of mere example, the microcontroller may command the sequential switching in of the capacitors through the bank without removing prior switched in capacitors, or command switching capacitors one at a time such that only one capacitor is in parallel circuit arrangement with the fixed and trim capacitors and additionally, the microcontroller may command that the capacitor selection proceed from the smallest to the largest value, to the next smallest to the next larger and so on until the maximum power delivery point is reached.

Furthermore in practice, once a maximum power delivery point is determined, subsequent determinations are made about such point. More specifically, if a check of the present power delivered reveals that it is, for example, less than 70% of the stored maximum value, the microcontroller will set the capacitor switches to an overall setting of that for the $32^{nd}$ position below the setting for obtaining maximum power and proceed to undertake the capacitor switching protocol through to the $32^{nd}$ switch position beyond the maximum power point. In the event that a switch setting cannot be obtained within such range to reestablish maximum power delivery, the microcontroller reinitiates the switching protocol from the beginning proceeding thereby through all the possible switch positions. Failing to achieve the maximum power delivery condition, the microcontroller issues an error message indicating a major malfunction, such as a disconnect of the inductor from the tuned circuit.

The frequency at which the capacitor adjustment process is undertaken as well as the time between capacitor switching during the maximum power determining process, may be set depending upon the expected nature of inductance value changes in normal operation. Nominally, the time to complete the full capacitor switching protocol is about 750 milliseconds and the time to the next determination of the tuned circuit operating point is one millisecond after establishing the capacitor switch setting that maximizes power delivery to the tuned circuit.

BRIEF DESCRIPTION OF THE DRAWINGS

The above and other aspects, features and advantages of the present invention will become apparent from the following more particular description thereof presented in conjunction with the following drawings, wherein:

FIG. 5A is a top view of an inductor of the embodiment of FIG. 1, showing an embedded inductor wire in phantom;

FIG. 5B is a cross-sectional view of the inductor of FIG. 5A taken along line 5B is a partial top view of the electric shield of the embodiment of FIG. 5;

FIG. 6A is a top view of an electric shield for mounting on the inductor of FIG. 5A;

FIG. 6B is an alternate embodiment of the shield of FIG. 6A;

FIG. 7 is a cross-sectional view of the inductor of FIG. 6C along lines 7-7;

FIG. 8 is a cross-sectional view of the left side of FIG. 7 with the base of the electric shield of FIG. 6A positioned midway along the outer side wall of the inductor;

FIG. 9 is a top view of the inductor of FIG. 5A including the electric shield of FIG. 6B;

DETAILED DESCRIPTION OF THE PREFERRED EMBODIMENT

Figure 1:
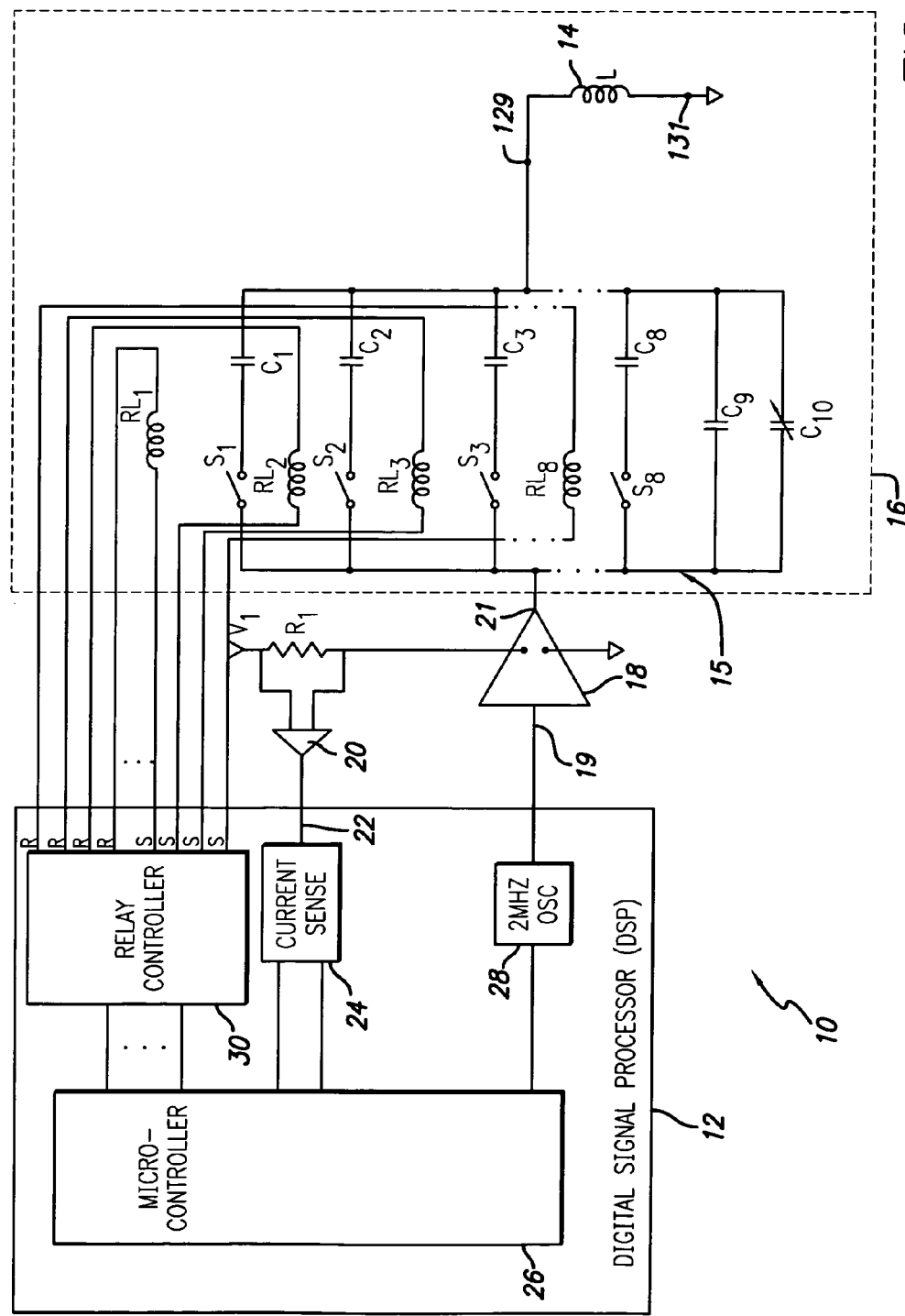
FIG. 1 is a schematic diagram of an embodiment of the automating tuning system of the present invention.

Referring now to FIG. 1 there is shown in schematic format, a block diagram of an embodiment of the present invention. The automatic tuning system 10 includes a digital signal processor (DSP) 12, a magnetic field generating inductor 14, a bank of switchable capacitors 15, a power amplifier 18 and a sense amplifier 20 that includes resistor R1. Broadly, the capacitor bank 15 and inductor 14 form a tuned circuit 16 having a resonant frequency that is determined by the value of inductance of inductor 14 and the capacitance value of the capacitor bank 15. The tuned circuit is driven by power amplifier 18 which obtains operating power from source V1 through resistor R1. The input 19 of power amplifier 18 is coupled to a reference oscillator 28 located on DSP 12. Although any of a number of reference frequencies may be considered, for the present invention, a reference oscillator frequency of 2 MHZ is preferable. By virtue of the connection of power amplifier 18 to the reference oscillator 28, an amplified signal, at the reference frequency, appears at the power amplifier output 21.

As is understood, maximum power transfer between the power amplifier 18 and the tuned circuit 16 occurs when the resonant frequency of the tuned circuit 16 equals the reference frequency. This occurs because the impedance of the tuned circuit 16 and therefore the load on the power amplifier 18 is at a minimum when the resonant frequency of the tuned circuit equals the frequency of the signal appearing at the power amplifier output 21. The voltage drop appearing across resistor R1 is a function of the power drawn by the power amplifier 18, which in turn is a measure of the current and therefore the power delivered by the power amplifier 18 to the tuned circuit 16. Accordingly, the voltage across R1 is applied to the input of differential amplifier 20 whose output 22 is applied to current sense module 24 located on DSP 12. As will be described later in more detail, under the control of microcontroller 26, the current sense module 24 monitors and compares the present value of the voltage drop across R1 to the just previous monitored value of such voltage drop as part of a technique to maintain the voltage drop across R1 at or within a range of maximum values. In practice, the amplifier 20, resistor R1 and associated circuitry are self contained on an integrated chip (IC), such as the commercially available Model 471 IC, manufactured by Maxim Integrated Products of Sunnyvale, Calif. The output signal of amplifier 20, provides a direct measure of the current supplied to the power amplifier 18 and therefore a measure of the power delivered by the amplifier 18 to the tuned circuit 16. It is to be understood that alternate techniques for detecting maximum power delivery by the power amplifier 18 are also contemplated by the present invention.

The primary source of the reference frequency of 2 MHZ is provided by oscillator 28 located on DSP board 12. The present invention contemplates a crystal oscillator having an inherent frequency of 16 MHZ and the use of dividers to provide division by eight to divide down the crystal oscillator frequency to a value of 2 MHZ. Crystal oscillators are commercially available and the technique of dividing down the crystal oscillator frequency by the use of dividers as well as other stable oscillator circuits are well within the knowledge of the skilled artisan and therefore will not be discussed here.

As previously mentioned, from a power delivery consideration, maximum power is delivered by the power amplifier 18 to the tuned circuit 16 when the resonant frequency of the tuned circuit 16 equals the frequency of the signal appearing at the power amplifier output 21. For the present embodiment the amplified signal appearing at the output 21 has a frequency of 2 MHZ and therefore for maximum power delivery to the tuned circuit 16, the resonant frequency of the tuned circuit 16 is adjusted until it reaches 2 MHZ. It is to be understood that the invention is not limited to operation at the stated reference frequency of 2 MHZ and that other reference frequencies are well within the contemplation of the present invention. As will be discussed below, automatic adjustment of the tuned circuit resonant frequency is desirable so as to compensate for variations in component value tolerances both for the capacitors in capacitor bank 15 as well as for variations in the inductance value of inductor 14. In an intended application, the inductor 14 is formed of a relatively flat thin flexible material upon which a series of closely spaced windings is placed. The windings are coated with a nontoxic insulating material to protect against direct contact with the windings. When the inductor 14 is in a flat profile and out of the proximity of objects such as metallic implements or flesh such as a human hand, the inductor 14 is characterized as having a fixed and unique inductance value. However, as the inductor is altered in profile when, for example, it is to be brought into proximity and conform to a region of a human body to which exposure of the magnetic field generated by the inductor is desired, the inductance value of the inductor may change, thereby changing the resonant frequency of the tuned circuit 16. Under such circumstance, the power delivered to the inductor and therefore the strength of the generated magnetic field could be significantly reduced. Accordingly the efficacy of the magnetic field could be severely compromised.

To continually and adaptively compensate for inductance value changes, the present invention utilizes a novel apparatus and method of capacitance value adjustment so as to maintain the resonant frequency of the tuned circuit 16 equal to the reference frequency. More particularly, the resonant frequency of tuned circuit 16 is maintained through the selective use of capacitors contained within capacitor bank 15 as well as capacitors C9 and C10. The capacitor's C1 through C8 are arranged so as to be in switchable parallel circuit arrangement with selected other capacitors in the bank 15. The resonant frequency of the tuned circuit 16 may be mathematically determined by the formula, $\omega_r = 1/\sqrt{LC}$, where $\omega_r$ is the resonant frequency of the tuned circuit 16 in radians per second and $\sqrt{LC}$ is equal to the square root of the effective inductance L of the inductor 14 multiplied by C which is the effective capacitance of the capacitor bank 15. From the equation, it is noted that changes in the inductance L may be compensated by changes in the capacitance C. Similarly, changes in the resonant frequency $\omega_r$, may also be adjusted and/or corrected by changes in the values of either or both the inductance L and capacitance C.

As is shown in FIG. 1, each capacitor C1 through C8 has an associated relay and relay switch. For example C1 is in series circuit arrangement with relay switch S1 which is activated by relay RL1. The relay RL1 has two states, such that when activated to be in the first state, S1 is closed and capacitor C1 is placed in parallel circuit arrangement with any other selected capacitors in the bank 15. Relay RL1 is activated to be in the first state (set) through the action of relay controller 30 located on DSP board 12. The microcontroller 26 provides the control command to the relay controller 30 regarding each relay and the state to be initiated for each such relay. To remove capacitor C1 from being in parallel circuit connection with other selected capacitors in the bank 15, RL1 is activated to be in a second state (reset) whereupon the switch S1 is opened thereby removing C1 from parallel circuit connection with other capacitors of the bank. To ensure the integrity of the switching process, activation of relay RL1 to the first state is caused by a current having a first polarity at the corresponding "S" and "R" terminals of the relay controller 30 and to the second state by a current having the opposite polarity at such "S" and "R" terminals.

In a like manner, the other capacitors in the bank 15, may be switched into and out of parallel circuit arrangement with the capacitors of the bank. Although the capacitor bank 15 has been described as having eight switchable capacitors, it is to be understood that a greater or lesser number of capacitors may be used depending upon design choice and desired tuning resolution and range.

The capacitors of the capacitor bank 15 are arranged such that the respective capacitance values are in binary progression format. The binary progression format is defined as $C(n) = C_i \times 2^{n-1}$ where $C_i$ equals the value of the first capacitor in the bank 15 and n is indexed from 1 to 8 representing the first to the eighth capacitor arranged in sequence. In the present invention, the first capacitor C1, has been selected to have a value of one (1) picofarad (pF). Accordingly, the next or second capacitor C2 in the sequence of capacitors in the bank 15 has a value of 2 pF, the third capacitor C3 in the sequence has a value of 4 pF, the fourth capacitor in the sequence has a value of 8 pF and so on until C8 is reached having a value of 128 pF. In the present example, when all the capacitor's C1 to C8 are included in parallel circuit arrangement, the total capacitance value is 255 pF. As previously mentioned two non-switchable capacitors are also provided namely fixed capacitor C9 and a variable trim capacitor C10, both connected between the power amplifier output 21 and inductor 14. The value of C9 is selected to set the resonant frequency of the tuned circuit 16 to less than the reference frequency based upon an expected nominal inductance value of inductor 14. Trim capacitor C10 is provided for initially adjusting the resonant frequency of the tuned circuit 16 to be lower than the reference frequency, by a desired amount. For the present application, the inductance of inductor 14 is about 12 microhenry (uH) and varies in the range from about 10 uH to 25 uH. Accordingly, the capacitor bank 15 including capacitors C9 and C10, should be capable of establishing a capacitance value of about 528 pF for a nominal setting and range from about 640 pF to 250 pF to accommodate the corresponding range of potential inductance values. For the present embodiment, C9 is selected to be 220 pF and C10 about 55 pF. In this manner capacitance must be added from the capacitor bank 15 to achieve obtaining a resonant frequency equal to the reference frequency. This provides the flexibility of adding and subtracting capacitance to the tuned circuit in order to achieve resonance.

Figure 2:
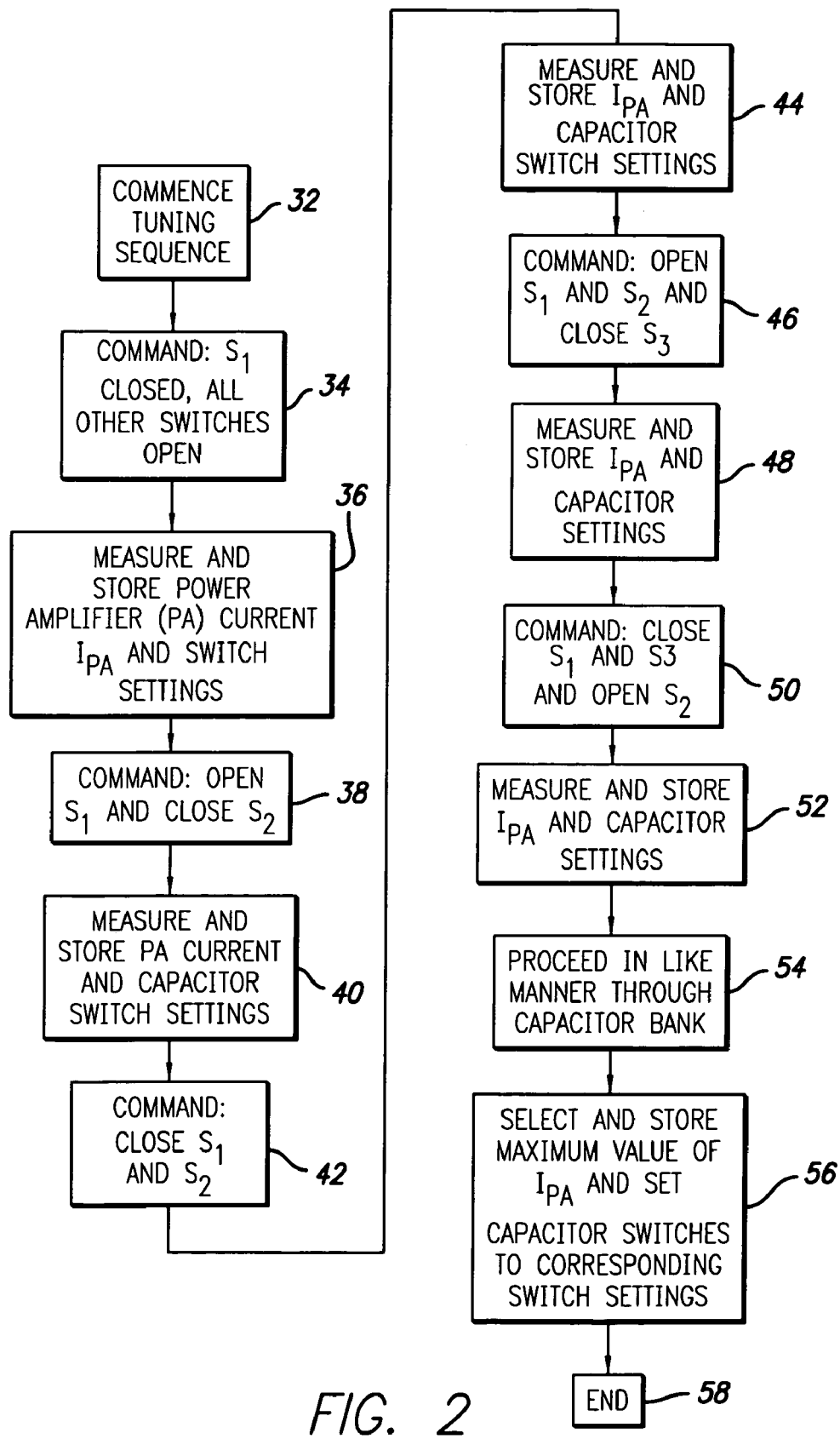
FIG. 2 is a flow chart of automatic tuning protocol of the embodiment of FIG. 1 to establish the capacitor switch settings to obtain maximum power delivery to the tuned circuit.

In practice and with reference to FIG. 2, the microcontroller 26, at block 32, initiates the tuned circuit tuning sequence. At block 34, the microcontroller 26 issues a command to the relay controller 30 to cause RL1 to close S1, and issues a command to all the other relays, RL2 to RL8, to open their respective switches S2 to S8 thereby removing capacitors C2 to C8 from parallel circuit connection with each other. At block 36, the current sensed and therefore the power delivered by the power amplifier 18 to the tuned circuit 16 is measured and stored in the microcontroller 26 along with the corresponding capacitor switch setting. In block 38, the microcontroller 26, then commands switch S1 to be opened and switch S2 to be closed. In block 40, the power amplifier current is measured and stored along with the corresponding capacitor switch setting. In block 42, S1 is closed and in block 44, the power amplifier current is measured and stored along with the corresponding capacitor switch setting. In block 46, switches S1 and S2 are opened and switch S3 is closed and in block 48, the power amplifier current is measured and stored along with the corresponding capacitor switch setting. In block 50, S1 is closed along with S3 and in block 52, the power amplifier current is measured and stored along with the corresponding capacitor switch setting. Proceeding in a like manner in block 54, the microcontroller 26 causes S2 to close and current measurements are made and stored along with the corresponding capacitor switch setting. On the next pass (not shown), microcontroller 26 causes switches S1 to S3 to open and switch S4 to close and so on through the entire capacitor bank until all switch combinations have been tested and the corresponding power amplifier current measured and stored along with the relative capacitor switch setting. The process of sequentially proceeding through the capacitor bank in the manner as just described may be referred to as "binary capacitor switching." Once all switch combinations have been tested, preferably using the binary capacitor switching technique, the microcontroller 26, in block 56, scans through all the combinations and sets the capacitor switches to the respective states that provides maximum power delivery to the tuned circuit 16 and in block 58, the sequence is ended. Inasmuch as the command issued in block 34 causes switch S1 to be closed and all other switches to be opened so as to establish an initial adjustable capacitor capacitance value, it is to be understood that the variable capacitor may be set to any arbitrary initial capacitance value with the tuning sequence proceeding thereafter through a range of capacitance values and preferably, but not necessarily, through all possible capacitance values, to determine the capacitance value that provides maximum power delivery to the tuned circuit 16. Additionally, the arbitrary initial setting of the variable capacitor is applicable to all embodiments of the invention described herein.

Figure 3:
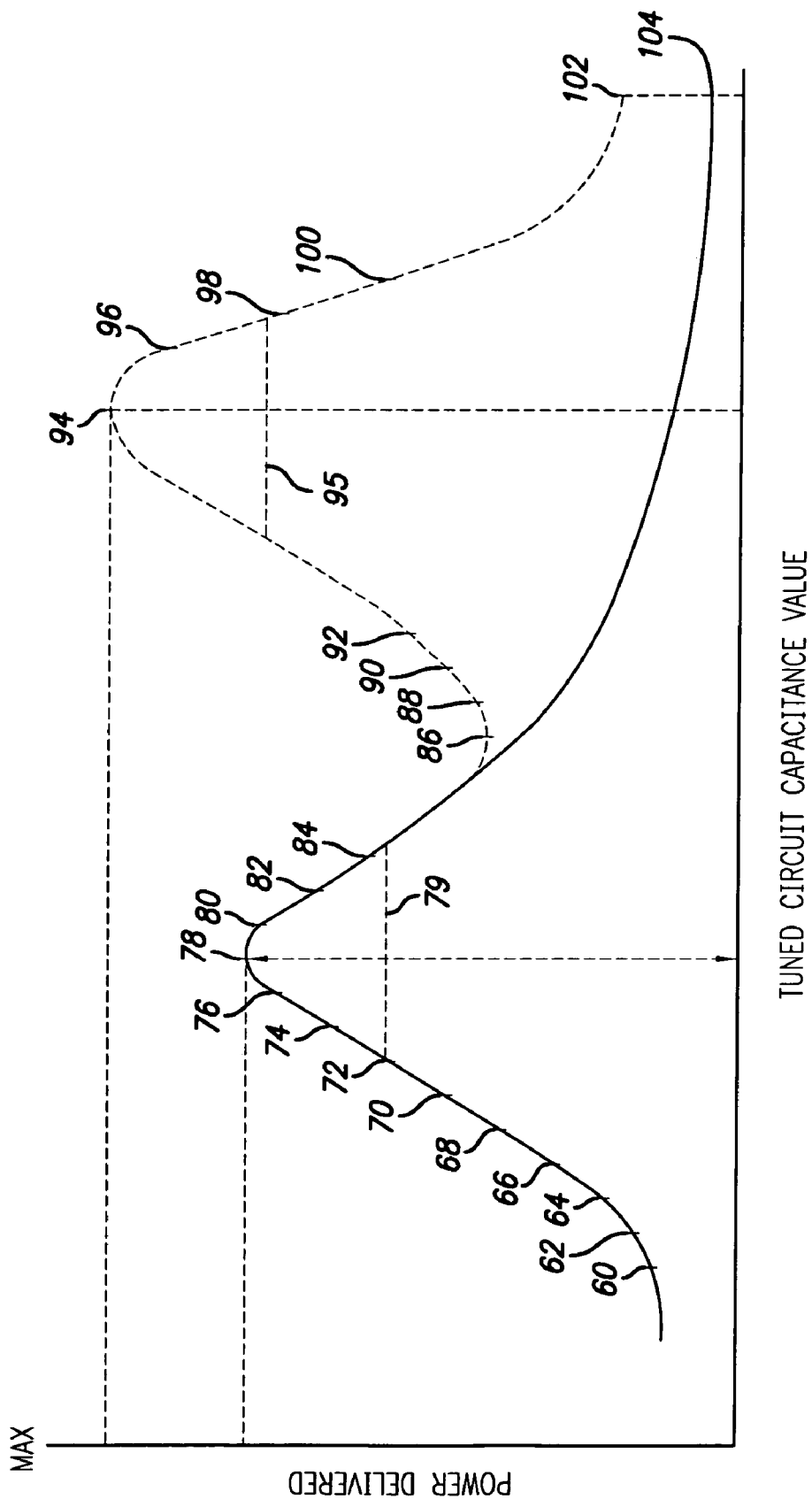
FIG. 3 is a graph depicting the power delivered to the tuned circuit versus the tuned circuit capacitance value for the embodiment of FIG. 2.

Although an apparent maximum power delivery point has been detected progressing through the binary capacitor switching technique, the microcontroller 26 nevertheless proceeds through all capacitor switch settings so as to identify all "maximum" power delivery points. The graphical representation of power delivered versus tuned circuit capacitance value shown in FIG. 3 illustrates the phenomena where multiple maximum (two or more) power delivery points are identified. For example, the switch position identified as 60 relating to only switch S1 being closed, shows operation at the initial point in the binary capacitor switching procedure. Switch positions 62 to 78 indicate relative switch settings and corresponding power delivery values as the microcontroller 26 proceeds to sequentially switch capacitors through the capacitor bank 15 in the binary capacitor switching manner previously described. It is observed that in this case, a first maximum is observed at switch position 78 and thereafter progressing from position 80 to 86, wherein further capacitance is added, the power delivery decreases. However, from position 88 to 94, power delivery increases to a second maximum at 94 and decreases from position 96 to 102 (both sections of the curve being shown in dotted line). For a single maximum power delivery point the final position 104 represents the condition where all capacitor switches are closed. In the event that only one maximum power point is detected, the expected terminus point would occur at the final position 104. The shape of the curves is merely illustrative of multiple "maximum" points and may vary in accordance with actual component values. In accordance with capacitor switching procedure just described, if the power delivered is described by a single maximum point such as position 78, then microcontroller 26 will command the appropriate capacitor switch settings to achieve tuned circuit operation at position 78. However in the apparent multiple maximum power delivery point situation, microcontroller 26 will command the appropriate switch settings to achieve tuned circuit operation at the highest "maximum" power delivery point and in the case shown in FIG. 3, at point 94.

Figure 4:
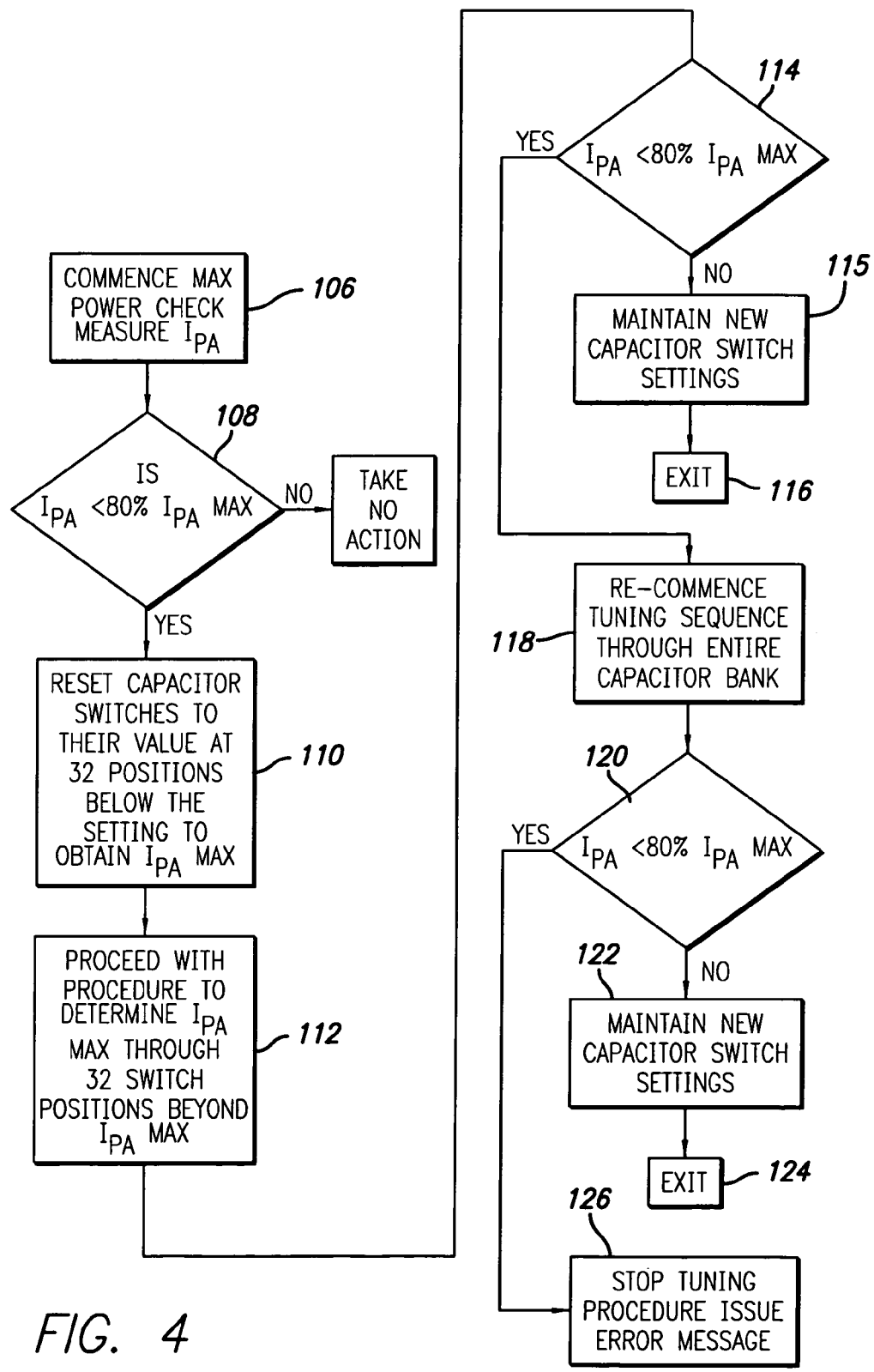
FIG. 4 is a flow chart of the embodiment of FIG. 2 to determine a capacitor switch setting to reestablish maximum power delivery to the tuned circuit.

Although the methods shown in FIGS. 2 and 4 describe sequentially adding and removing adjacent capacitors in the bank 16, it is to be understood that numerous other sequences for capacitor switching are also contemplated by the present invention. As a mere example, switching every second capacitor in a series rather than every adjacent capacitor may be used.

As previously described, changes in the inductance value of inductor 14, may cause a change in the resonant frequency of the tuned circuit 16 away from the reference frequency, with the corresponding decrease in power delivery to the tuned circuit. To ensure continual maximum power delivery, microcontroller 16 undertakes periodic tests to monitor the power delivery to the tuned circuit 16. Accordingly, and with reference to FIG. 4, the microcontroller 26 commences the maximum power check at block 106. In block 108, a test is made as to whether the current supplied to power amplifier 18 and therefore the power delivered to the tuned circuit 16, is less than 80% of the initially determined and stored maximum current (delivered power below dotted lines 79 or 95 in FIG. 3). If in the negative, then no action is taken. However, if in the affirmative, then in block 110, the microcontroller 26 adjusts the capacitor switches to a switch setting that is a fixed number of positions below that initially required to cause maximum power delivery. For the embodiment of FIG. 4, the fixed number of switch settings is 32. In block 112, microcontroller 26 proceeds to undertake the binary switching technique through the capacitor bank 15 to a switch setting that is 32 positions beyond that required to initially cause maximum power delivery to the tuned circuit 16. In block 114, a test is made as to whether any power amplifier current obtained in any of the 64 switch settings is within 20% of the stored maximum value and if so, in block 115, the corresponding switch settings corresponding to such power amplifier current, is commanded and maintained and the sequencing is terminated at block 116.

In the event none of the power amplifier current values are within 20% of the maximum stored value through the 64 switch settings commanded, as determined in block 114, then in block 118, microcontroller 26 recommences the tuning sequence through the entire capacitor bank. In block 120, a test is made as to whether any power amplifier current obtained in any of the 256 switch settings exceeds a predetermined threshold value, is within 20% of the stored maximum value and if so, the corresponding switch setting corresponding to such power amplifier current, is commanded and maintained and the sequencing is terminated at block 124. In the event none of the power amplifier current values are within 20% of the maximum stored value, as determined in block 120, then in block 126, microcontroller 26 terminates the sequence and provides an error message. This situation would occur if, for example, the inductor coil became electrically disconnected from the tuned circuit. Although the present discussion describes a threshold of 80% in blocks 114 and 120 with a corresponding inclusion range of 20%, it is to be understood that these values are not to be taken in a limiting sense and that other thresholds and corresponding inclusion ranges such as for example, 70% and 30% respectively, are within the contemplation of the invention.

Referring now to FIG. 5A, there is shown a top view of an embodiment of the inductor 14 utilized in the present invention. The inductor 14 is configured having a somewhat "peanut" shaped cross-section or modified "horse race track" shape, so as to conform to the shape and contour of the region around a patient's neck in the area just below the chin. The intended application for such inductor shape is for communication and power delivery, via magnetic fields generated by the inductor 14, with microdevices implanted in the patient's neck around and below the chin. It is to be understood and within the contemplation of the present invention, that inductor shapes may take on various geometries dependent upon the nature and requirements of the particular application. In that regard, the inductor may, as mere examples, be configured as a square or rounded or elliptical in shape. The inductor 14 includes a single conductor 128 wound in a series of concentric windings to form an inductor coil. Electrical connection of the inductor 14 to the tuned circuit 16, is made via terminals 129 and 131 connected to respective ends of the conductor 128. The conductor 128 preferably is formed of a commercially available wire designated as a LITZ wire and characterized as having about 150 strands of 44 gauge electrically conductive wire encased in a silk sheath. An advantage of such wire is that by virtue of the small AC resistance of the wire, very little heat is generated due to exposure of the wire to the magnetic fields generated by the inductor 14. Preferably, the diameter of the wire appropriate for use in the inductor is in the range of 1 mil to about 250 mils. The conductor 128 is embedded within a flexible, nontoxic, medical grade material 130, such as silicone. As is shown in the cross-sectional view of FIG. 5B, the conductors lay in a plane P defined by such conductors, and in doing so, the potential of generating a more uniform magnetic field is enhanced. Material selection was made in order to minimize any unwanted and stray capacitances that are a concern with systems involving electrically conductive elements.

To further limit the influence of external contributions to stray capacitance on the inductor 14, a shield 132, such as a Faraday shield, is wrapped around the inductor 14. The shield 132 is designed to negate the effects of electric fields without affecting the alternating magnetic fields. The shield 132, shown in FIG. 6A in a flat extended top view, includes a plurality of alternately oppositely extending fingers 134 and 136 that extend essentially orthogonally from a lateral strip or base 138. Preferably, the shield 132 and the other shields described below, are formed from a copper plated polyester fabric shielding tape with sufficient flexibility and elasticity so that the fingers 134 and 136 may be alternately wrapped around the inductor 14 and normal bending of inductor 14 will not cause the shield to rupture. Alternate shield designs are also contemplated by the invention intended to resist rupture upon bending of the inductor 14.

Figure 6C:
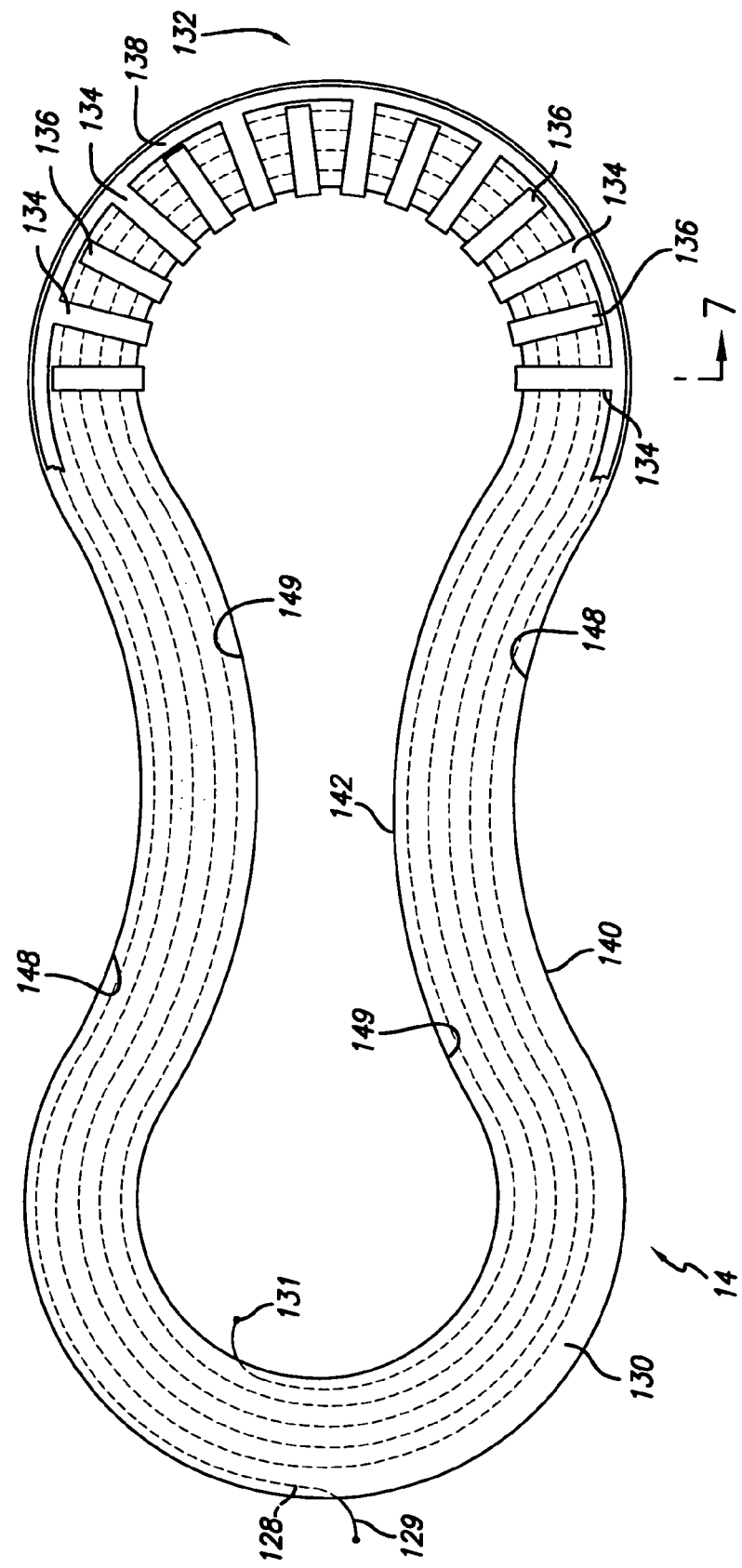
FIG. 6C is a top view of the inductor of FIG. 5A including the electric shield of FIG. 6A

As is shown in FIG. 6C, a shield 132 is placed on inductor 14 with the base 138 located in proximity to and along the inductor outer edge 148. The base 138, as well as the finger's 134 and 136, may be held in place by using any one of a number of known adhesives appropriate for medical applications. As is illustrated in the cross-sectional view of FIG. 7, the fingers 134 and 136 are sized so that they may be completely wrapped around the region between and including the inductor's outer side wall 140 and inner side wall 142, so as to establish a sequence of closely spaced fingers that provide a very effective electric shield against the effects of unwanted stray capacitances. The size of the fingers and the spacing between them as shown in FIGS. 6A and 6B, have been enlarged for purposes of clarity. Although the fingers 134 and 136 are completely wrapped around the inductor 14, they are sized in length so each respective end may come into close proximity to, but not contact, base 138. As discussed later in detail, an alternate positioning of the base 138 is to be in proximity with and along the inductor's outer side wall 140. Although FIG. 6C shows only a portion of the shield, it is to be understood that the shield 132 completely envelopes the inductor 14.

With regard to placement of the shield 132 on the inductor 14, FIG. 6C shows an embodiment wherein the base 138 is positioned adjacent to the inductor outer edge 148. An alternate embodiment of the invention shown in FIG. 6C only as it pertains to the orientation of the shield 132, is shown in FIG. 8, where the base 138 is positioned to lie along the inductor outer side wall 140 between inductor surfaces 151 and 153. In this manner, concerns regarding fracture of the material forming the base 138 due to repeated twisting of the inductor in preparation for and during use, are alleviated. As noted, the cross sectional view of the assembled inductor 14 shown in FIG. 7, illustrates the alternating wrapped configuration of the fingers 134 and 136. Although FIG. 8 shows the shield base 138 positioned along the outer side wall 140, it is to be understood that, as an alternative, the base 138 may also be positioned along the inner side wall 142 with the fingers 134 and 136 wrapped around inductor surfaces 151 and 153 respectively, in a manner similar to that shown in FIG. 8, to achieve similar shielding advantage. As a further enhancement to the inductor structure, the entire inductor including the shield, may be embedded within a nontoxic medical grade material 144, such as silicone. This provides additional protection to the shield from dislodgement from the inductor as well as providing protection from the effects of continual handling by a patient.

Figure 10A:
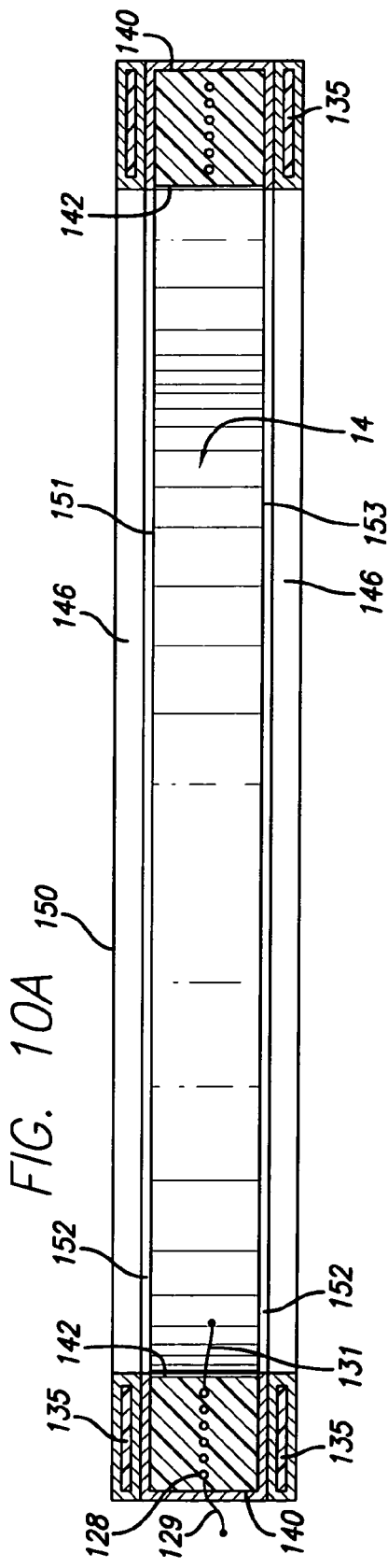
FIG. 10A is a cross-sectional view of an embodiment of the present invention taken along lines 10A in FIG. 9 including a shielding plate positioned between the inductor and the electric shield of FIG. 6B.

An alternate embodiment of the above described inductor assembly is shown in FIG. 9. More specifically, the shield (shown in solid lines for clarity and understanding of placement of the shield with respect to the structure of inductor 14) conforms to the shield 137 shown in FIG. 6B. A shielding plate 146 (see FIGS. 10A and 10B), formed preferably from a nontoxic medical grade material such as capton, has a geometry that essentially conforms to the shape of inductor 14. As is shown in FIG. 10A, an electric shield 137 is disposed completely along and embedded within the shielding plate 146 just below the surface 150 of the shielding plate. The shield 137 is positioned on the inductor 14 so that the shield base 139 is in proximity with and runs along the inductor outer edge 148 (se FIG. 9) with the fingers 135 extending inwardly in a direction across inductor surface 151 toward the inductor inner edge 149. A second shield 137 is positioned in a similar manner on the opposite side of the inductor 14 such that the fingers extend across inductor surface 153. The characteristics and construction of shield 137 as shown if FIG. 6B, conforms essentially to that for shield 132 except that the fingers 135 are sized to extend only across respective inductor surfaces 151 and 153.

As is shown in FIG. 10A, inductor 14 is sandwiched between two identical spacers 152 that is further sandwiched between two shielding plates 146. The spacers 152 are formed of a material having a low permitivity or a dielectric constant close to that of a vacuum or air, such as neoprene that contributes, little or no stray capacitance to the overall inductor coil structure. To provide enhanced shielding, the shield 137 contained within respective shielding plates 146, are electrically interconnected by means of electrical conductor 154. In this manner the shielding plates provide a very effective electric shield for the inductor 14. In a manner similar to that for the embodiment of FIG. 5, the elements of the inductor configuration of FIG. 10A may be secured together with known medical adhesives or encased, for example, within a flexible nontoxic material such as silicone. The above described inductor thus provides a relatively flexible, reliable and electrically shielded element for use in a magnetic field generating tuned circuit.

Figure 10C:
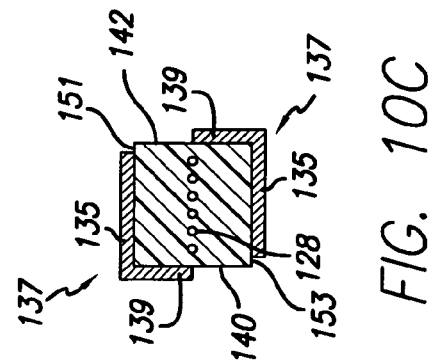
FIG. 10C is a cross-sectional view of the left side of FIG. 9 with the base of one electric shield positioned on the outer side wall of the inductor and the base of the other electric shield positioned along the inner wall of the inductor.
Figure 10B:
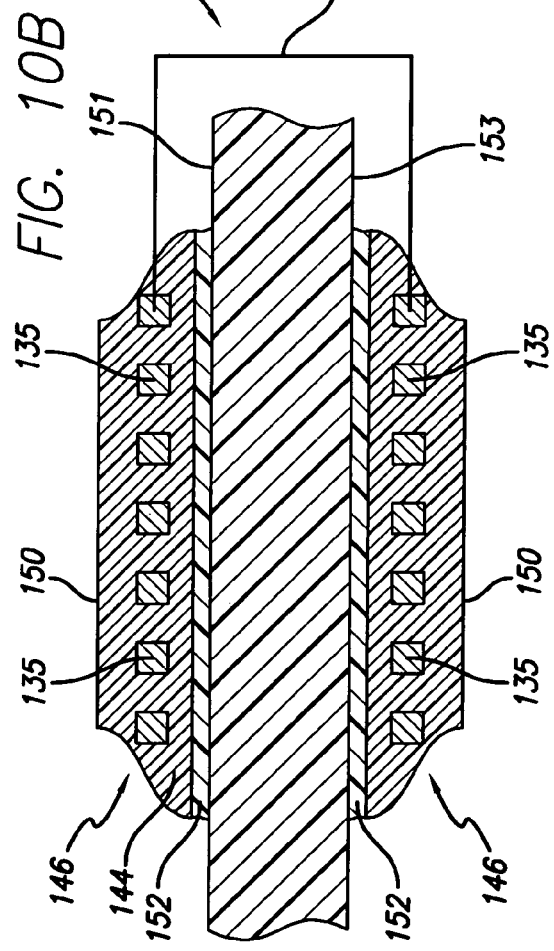
FIG. 10B is a partial cross-sectional view of an embodiment of the present invention taken along lines 10B of FIG. 9.

As shown in FIG. 10A, the inductor 14 has an essentially rectangular edge wise cross-section in which conductor 128 is disposed between the outer side wall 140 and the inner side wall 142 of inductor 14. Conductor terminals 129 and 131 are connected to the tuned circuit 16 as shown in FIG. 1. The shielding plates 146 enclose spacers 152 which further encloses the inductor 14. As shown in FIG. 10C, to alleviate any concerns regarding the fracturing of the shield base 139 as a result of repetitive bending of inductor 14, the base 139 of one shield may be positioned along outer side wall 140 with its corresponding fingers 135 extending across inductor surface 151 and the base 139 of a second shield may be positioned along inner side wall 142 with its corresponding fingers 135 extending across inductor surface 153. As is shown in FIG. 10B, each of the shield's 137 may be electrically connected together to enhance the overall shielding capability of the shields.

Although the present invention has been described in terms of a switchable capacitor bank, it is to be understood that other variable capacitor techniques are also contemplated by the present invention. For example, as earlier described, a motor driven variable capacitor may be used in place of the capacitor bank 15. The motor may be either a continuous drive or stepper motor under the control of the microcontroller 26. In such case, the relay controller 30 would instead drive the motor, under the command of microcontroller 26, to a position that provides a capacitance value of the variable capacitor, that maximizes the power delivered by power amplifier 18 to the tuned circuit 16. In the case of a stepper motor embodiment, the motor would index the variable capacitor through a range of discrete capacitance values to determine a capacitance value that maximizes the power delivered by power amplifier 18 to the tuned circuit 16.

Figure 11:
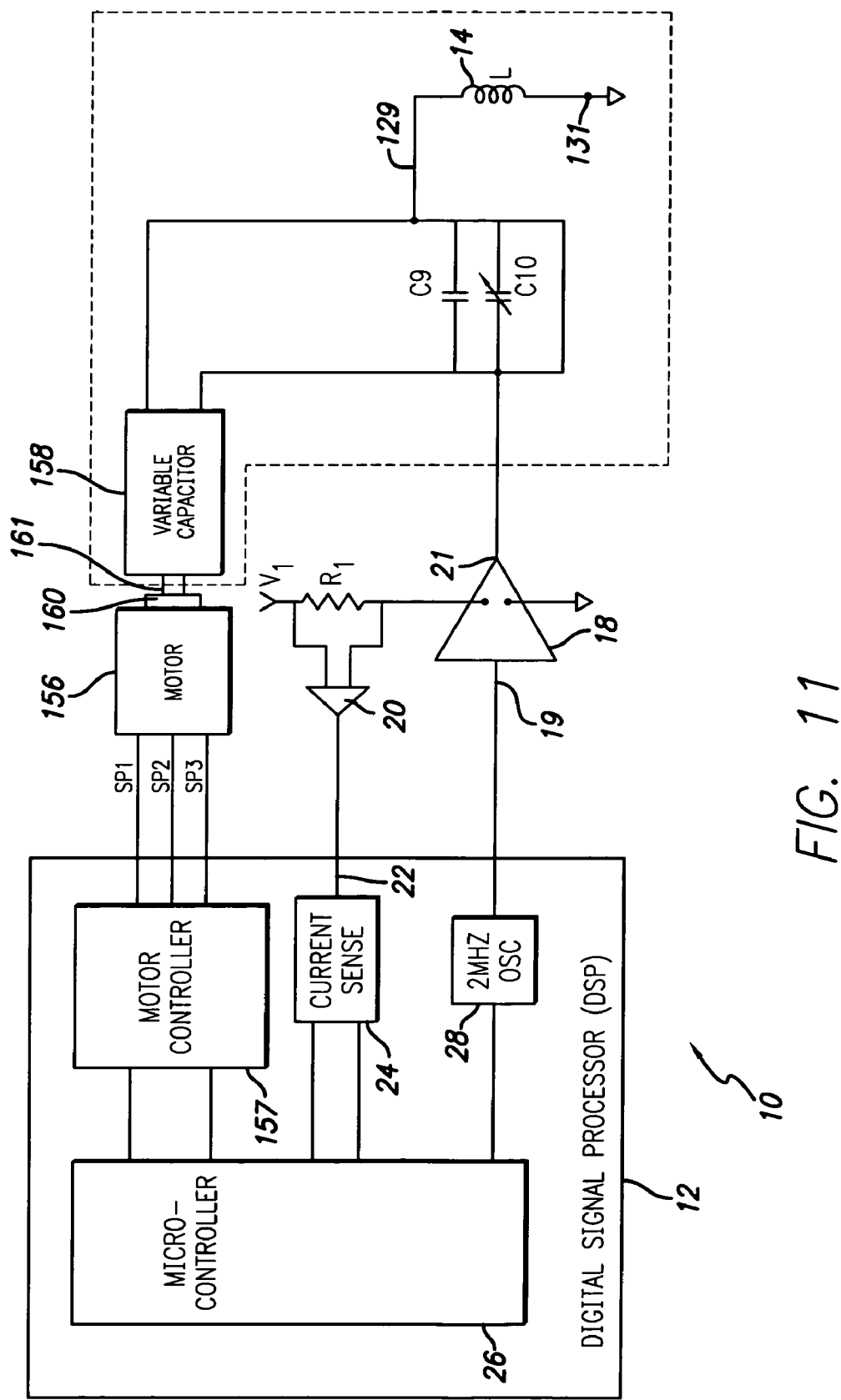
FIG. 11 is a schematic diagram of an alternate embodiment of the present invention showing a motor driven variable capacitor.

As an example, FIG. 11 shows an alternate embodiment of the present invention utilizing a motor driven a variable capacitor in the tuned circuit. More specifically, motor 156 drives a variable capacitor 158 through a reduction gear assembly 160. A candidate motor 156 and gear assembly 160 are commercially available from Smoovy® Micro Precision Systems, which is part of RMB SA of Switzerland. Although the present invention includes a reduction gear assembly driven by the motor, it is to be understood that the invention also contemplates direct drive of the variable capacitor, by the motor 156, without the use of a gear reduction assembly. An appropriate device for the present invention is identified as Smoovy® Gear Motor Model No. SPE 59007 and the reduction gear ratio associated with such gear motor, is 625:1, so that 625 full rotations of the motor shaft (not shown) will cause one full rotation of the gear assembly output shaft 161. The output shaft 161 is mechanically coupled to a rotatable shaft (not shown) of variable capacitor 158 such that when the shaft is rotated, the capacitance value. of the variable capacitor 158 is caused to change in a controlled manner. A variable capacitor appropriate for the present invention is commercially available, from the Valtronics Corporation of Danville, N.J., under the part number AJ555HV. The capacitor is a multi-turn PTFE dielectric, variable capacitor having a capacitance range from below 1.5 pF to above 55.0 pF through a total of 26 turns of the capacitor's rotatable shaft.

The motor 156 described above is a bidirectional brushless DC motor having three stator poles SP1, SP2, and SP3 coupled to the motor controller 162 as shown in FIG. 11. Accordingly, for rotation of the motor shaft in a first direction, the stator poles are electrically pulsed, under the control of the microcontroller 26 and motor controller 157 in a first sequence, that is, electrical pulses are applied sequentially to stator poles SP1, SP2, and SP3. For rotation of the motor shaft in a direction opposite to the first direction, the stator poles are electrically pulsed in a second sequence opposite to the first sequence, that is, electrical pulses are applied sequentially to stator poles SP3, SP2 and SP1. The stator poles are configured in a "Y" arrangement, requiring a total of six pulses, two per pole, to provide one complete motor shaft rotation or equivalently each pulse provides a 60° rotation of the motor shaft.

In practice, obtaining operation of the tuned circuit 16' at the resonant frequency equal to the reference frequency follows a process similar to that shown in FIG. 2. More specifically and with reference with FIG. 12, the microcontroller 26 commences the tuning sequence in block 162. In block 164, microcontroller 26 causes motor 156 to drive the variable capacitor 158 to one end of its operating range, that is, the initial point of its 26 turn travel. Next in block 166, microcontroller 26 causes the motor controller 157 to pulse the motor 156 so as to drive the variable capacitor 158 through its entire range of capacitance values. In doing so, the current drawn by power amplifier 18 from source V1 and therefore the power delivered to the tuned circuit 16' by the power amplifier 18 is measured corresponding to each delivered stator pulse. Accordingly, in block 168 a matrix or table is stored in microcontroller 26 that relates the power delivered to the tuned circuit 16' by the power amplifier 18, corresponding to each respective delivered stator pulse. Subsequent to progressing through the entire range of variable capacitor capacitance values, the microcontroller 26, in block 170, examines all stored values of the power/current delivered by power amplifier 18 and identifies the largest power/current value and the corresponding stator pulse count.

Further in block 170, microcontroller 26 causes the motor 156 to be pulsed the appropriate number of pulses to restore the power delivery to the tuned circuit 16' to the maximum value determined. Once the variable capacitor has been adjusted to provide tuned circuit resonance, the microcontroller 26 makes periodic checks of the power delivery for the purpose of maintaining maximum power delivery by the power amplifier 18. In the event that the microcontroller 26 detects that the power delivery has dropped below a preselected value relative to the maximum value, the microcontroller 26 undertakes reestablishing maximum power delivery. Although a wide range of preselected values is contemplated by the present invention, preferably the microcontroller 26 will attempt to reestablish maximum power delivery when the value of the delivered power drops below 80% of the maximum value. In reestablishing maximum power delivery, the microcontroller 26 selects a range, preferably equal to 1/8 of the overall range of the capacitance values of variable capacitor 158, through which it attempts to reestablish maximum power delivery. Accordingly, microcontroller 26 commands delivery of the number of stator pulses required to drive the variable capacitor 158 to a capacitance value equal to 1/16 of the total capacitance range below the original capacitance value to achieve resonance to a capacitance value equal to 1/16 above the original capacitance value to achieve resonance.

Figure 12:
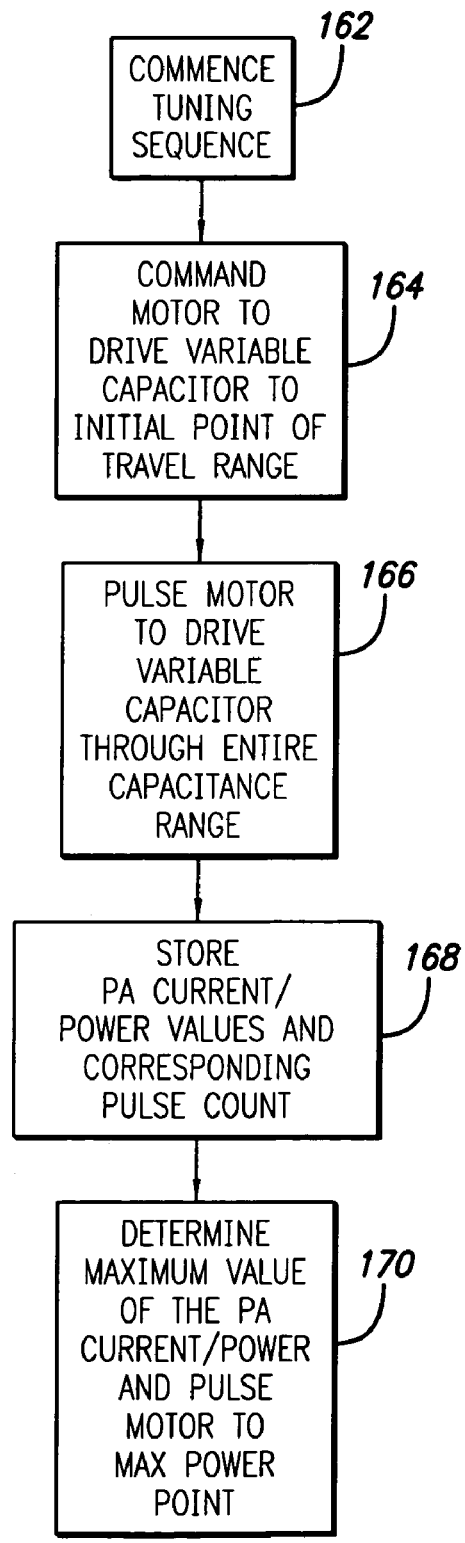
FIG. 12 is a flow chart of automatic tuning protocol of the embodiment of FIG. 11 to establish the capacitor position to obtain maximum power delivery to the tuned circuit.
Figure 13:
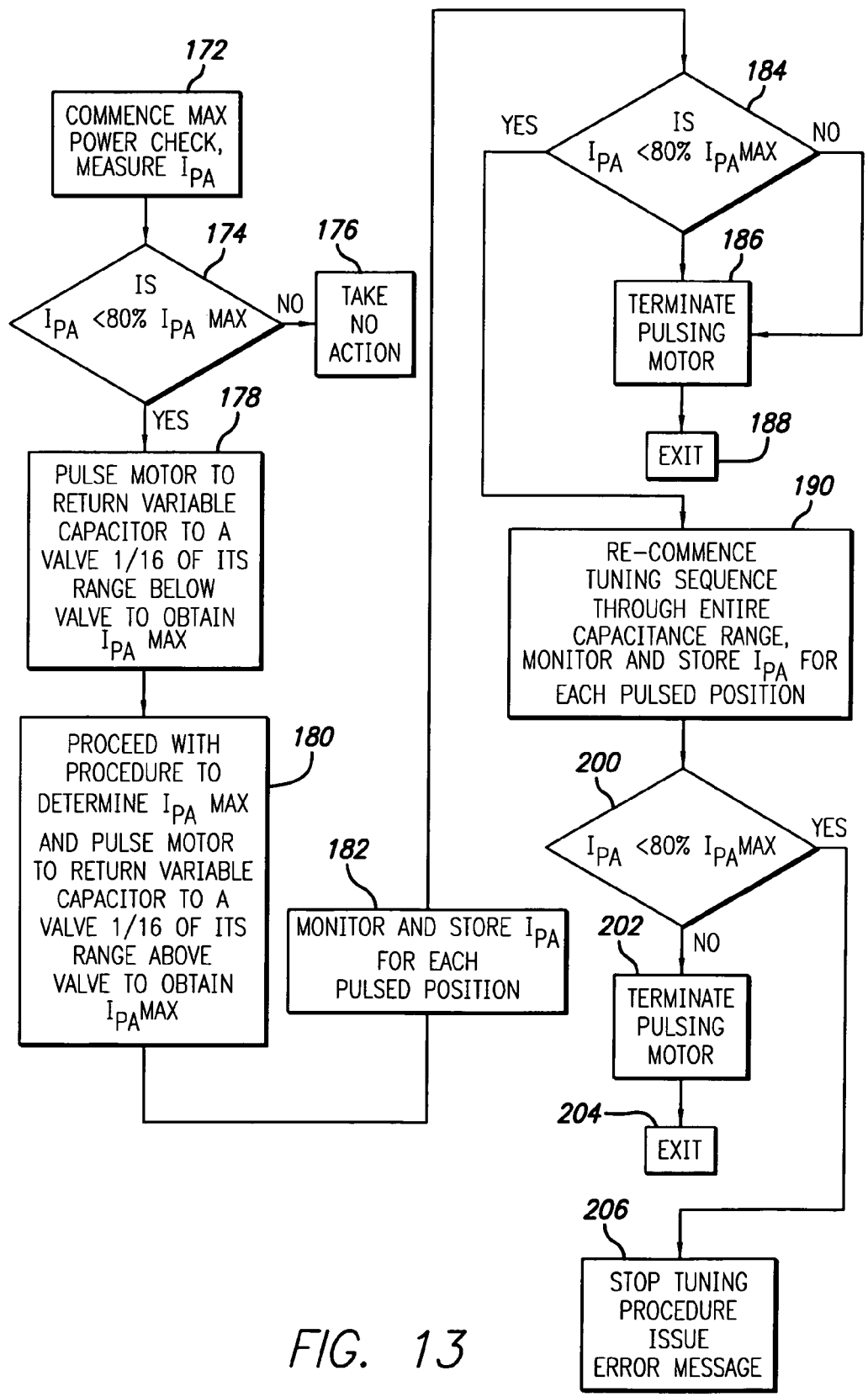
FIG. 13 is a flow chart of the embodiment of FIG. 11 to determine a capacitor position to reestablish maximum power delivery to the tuned circuit.

If resonance is not reestablished, then microcontroller 26 recommences the tuning sequence as shown in FIG. 12, using the full range of capacitance values of variable capacitor 158. Although the preferred embodiment of the present invention utilizes the full range of capacitance values of the variable capacitor 158, it is to be understood that smaller ranges are within the contemplation of the invention. Moreover, in the process of reestablishing resonance, the same criteria utilized in the embodiment of FIG. 1 may be used where a resonance point is accepted if the power delivered by power amplifier 18 is within 20% of the previously determined maximum value. In that regard, the above process is shown in FIG. 13.

More specifically, the microcontroller 26 initiates the tuning sequence in block 172 and then in block 174, checks whether the current delivered to power amplifier 18 is less than a predetermined percentage of the originally determined maximum value of the delivered current. Since the current delivered to the power amplifier 18 is a measure of the power delivered by the power amplifier 18 to the tuned circuit 16', such current may be used as a control parameter in the tuned circuit tuning procedure. As is shown in block 174, although other values are within the contemplation of this invention, the predetermine percentage for the present invention was selected as 80%. If the present value of the power amplifier input current is greater than 80% of the maximum value of the input current, then in block 176, no action is taken. Otherwise, in block 178, the microcontroller 26 causes the motor 156 to be pulsed so as to position the variable capacitor 158 to have a capacitance value that is a fraction of the entire capacitance range below the capacitance value that resulted in the maximum power delivery to the tuned circuit 16'. Although a wide range of values may be used, for the present invention a value of 1/16 of the entire capacitance range is preferable. In block 180, the motor 156 is then pulsed to drive the variable capacitor 158 through a continuous range of values to a value of capacitance that is 1/16 above the value that resulted in the maximum power delivery to the tuned circuit 16'.

In block 182 each value of power amplifier current is monitored and stored and when the power amplifier current has a value that is greater than 80% of the original maximum value (block 184), the process terminates (blocks 186 and 188). If however, the power amplifier current does not achieve a value that is greater than 80% of the original maximum value, then in block 190 the microcontroller 26 causes the tuning sequence to recommence through the entire range of variable capacitor capacitance values. In proceeding through the entire range of capacitance values, the microcontroller 26 causes the tuning sequence to terminate when a value of the power amplifier current is greater than 80% of the original maximum value (blocks 202 and 204) and if the power amplifier fails to reach such value, the microcontroller 26 terminates the tuning sequence and issues an error message.

Figure 14:
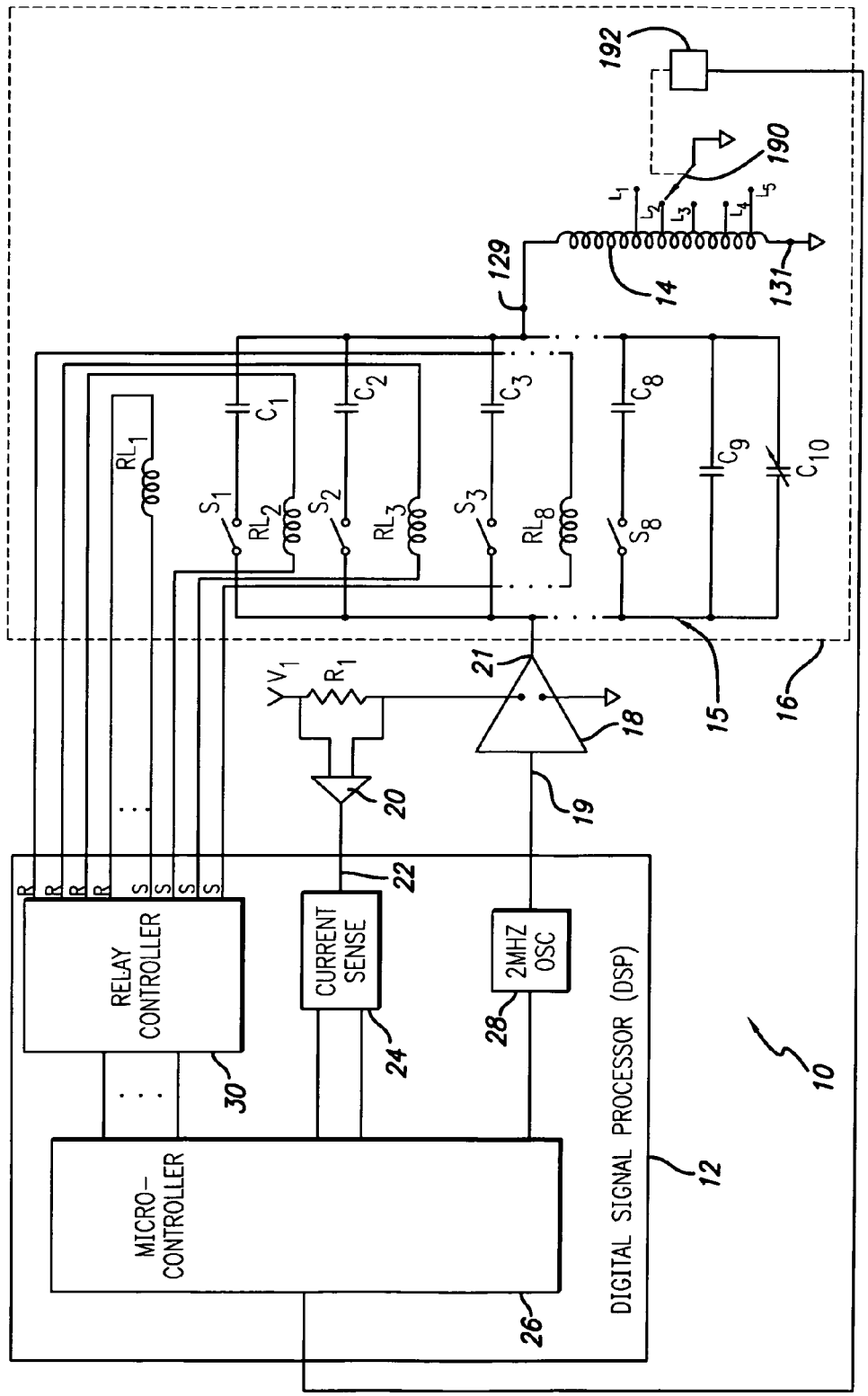
FIG. 14 is a schematic diagram of an alternate embodiment of the automatic tuning system of the present invention.

A still further alternate embodiment of the present invention is shown in FIG. 14 wherein the inductor 14 includes a number of taps, illustratively shown as L1 to L5 that are attached to preselected points along the inductor wire 128. A larger or fewer number of taps is also contemplated by the invention depending upon a desired level of resolution, with a greater number of taps providing greater resolution. By connecting the taps at the various points along the inductor wire 128, different inductance values corresponding to each tap are obtainable because a different length of inductor wire, each of which providing a different inductance value of the inductor, is selectable by switch 190. The taps are selectively connected to ground through switch 190 which is controlled by switch actuator 192. Although shown as a mechanical switch arrangement, it is to be understood that the switch 190 may be replaced by an equivalent switching arrangement utilizing semiconductor devices such as transistors coupled to each respective tap and that are selectively rendered conductive or non-conductive as the case may be, under the control of microcontroller 26. Still another switching arrangement may include a relay activated switching arrangement similar to that shown in FIG. 1 wherein each respective switch (in a manner similar to S1 to S5) is connected between a respective inductor tap (L1 to L5) and ground. The opening and closing of a switch may be controlled by microcontroller 26 in the manner previously discussed for the embodiment of FIG. 1.

As was previously noted, the resonant frequency of the tuned circuit 16 may be adjusted by changing the inductance value of inductor 14 as well as the capacitance value of the capacitor bank 15. Adjusting the inductance value of inductor 14 may be accomplished by connecting switch 190 to a selected tap. In practice, the microcontroller 26 may command the actuator 192 to initially position the switch 190 at L5 which provides the maximum inductance value of inductor 14 and then commence the tuning sequence as shown in the flow chart of FIG. 2. Failing to achieve a maximum value of power amplifier current, at block 56, the microcontroller 26 may command the switch actuator 192 to position the switch 190 at L4 which lowers the effective inductance in the tuned circuit 16 and the tuning sequence of FIG. 2 is repeated and so on until maximum power delivery to the tuned circuit 16 is obtained. Similarly for the maximum power check shown in the flow chart of FIG. 4, at such time as the power amplifier current fails to attain a value greater than 80% of the current determined in block 120 of FIG. 4, then rather than immediately proceeding to block 126 where the tuning procedure is terminated, the microcontroller 26 commands the actuator 192 to index to the next inductor tap in the series and the power check is repeated at block 106. At such point that the power amplifier current exceeds 80% of the previously determined maximum power amplifier current, then in addition to maintaining the new capacitor switch settings called for in block 122, the microcontroller 26 maintains the switch 190 at the position which resulted in obtaining such maximum current. In the event that the power amplifier current fails to attain a value that is 80% of the maximum power amplifier current value after switching through all the inductor taps, then control transfers to block 126 wherein the tuning sequence is terminated and an error message is issued at block 126. To provide the capability of initially either increasing or decreasing the inductance value, the initial position of switch 190 may be set at L3. In such case the microcontroller 26 may command the switch 190 to either increase or decrease the effective inductance value by commanding the switch to taps L4 or L3 respectively, depending upon the value of delivered power.

In a similar fashion, the embodiment of FIG. 11 may also include an inductor tap circuit as just described for the embodiment of FIG. 1. Still further, the process of obtaining the maximum value of the power amplifier current as shown in the flow chart of FIG. 12, may also include the steps of repeating the tuning sequence for each setting of switch 190 through the inductor tap's L1 to L5. And in yet still another similar fashion, achieving a power amplifier current of greater than 80% of the previously obtained maximum value also includes repeating the steps shown in the flow chart of FIG. 13, for each setting of the switch 190.

Although the technique described for monitoring power transfer from the power amplifier 18 to the tuned circuit 16 relies upon monitoring the current through resistor R1, maximum power transfer may also be monitored by measuring the current in the inductor 14. This may be accomplished, for example, by tapping off a portion of the inductor winding (in a manner as was described for taps L1 to L5) and applying the monitored signal to a rectifier circuit to obtain a measure of a maximum value thereof in a manner similar to that described for the embodiment of FIG. 1. The rectifier circuit may include conversion circuitry to convert the monitored signal to a signal indicative to inductor current. The monitoring process may include a voltage monitor as well as a current monitor (for example, as previously described) such that inductor current detection is selected to occur at such time that the inductor voltage is at a zero crossing. Since the inductor voltage is 90 degrees out of phase with the inductor current, monitoring at the inductor voltage zero crossing provides the opportunity to monitor the value of the inductor current when it is at a maximum value for the present tuning circuit resonant frequency.

Figure 15:
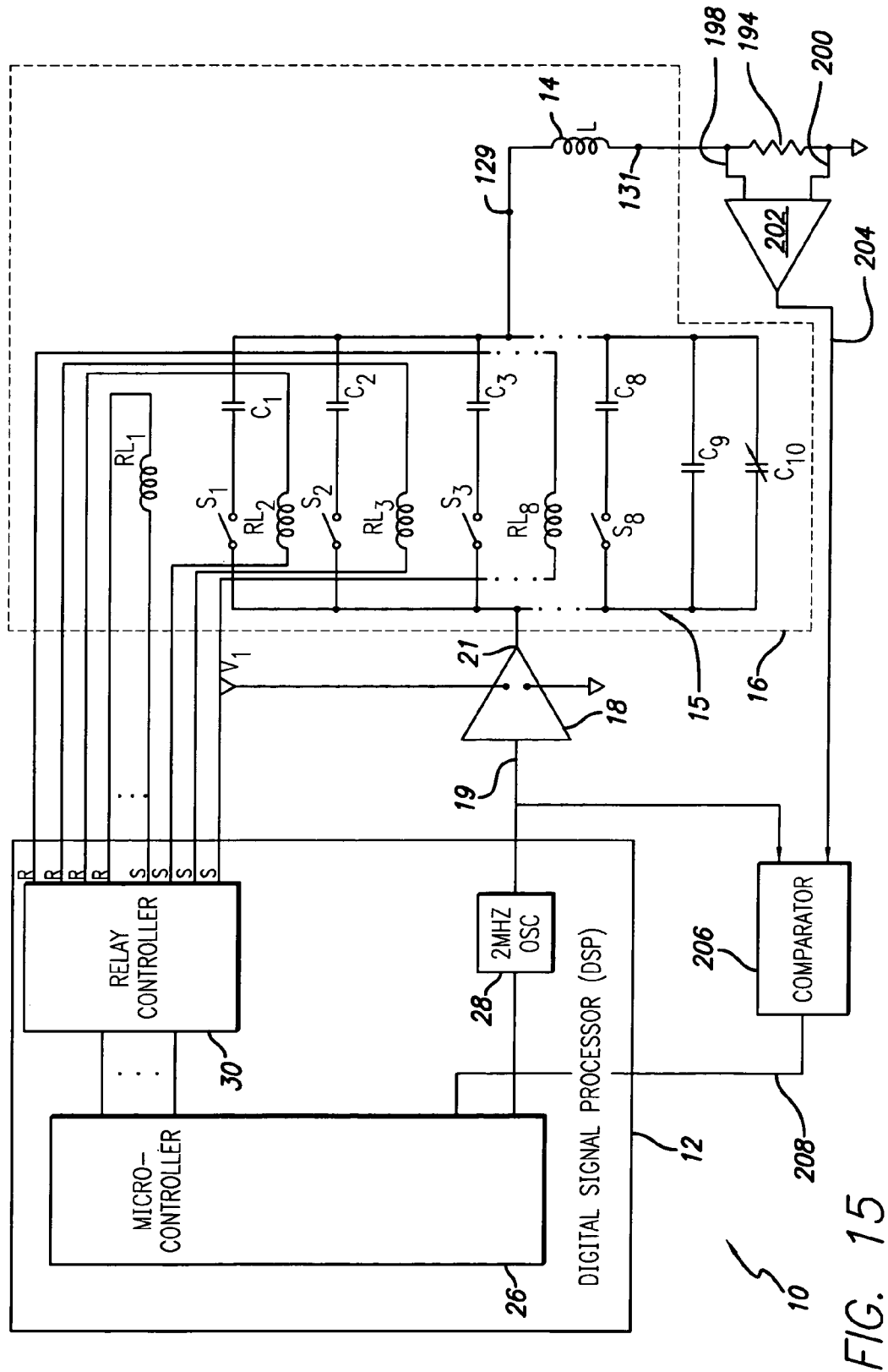
FIG. 15 is a schematic diagram of an alternate embodiment of the automatic tuning system of the present invention.
Figure 16A:
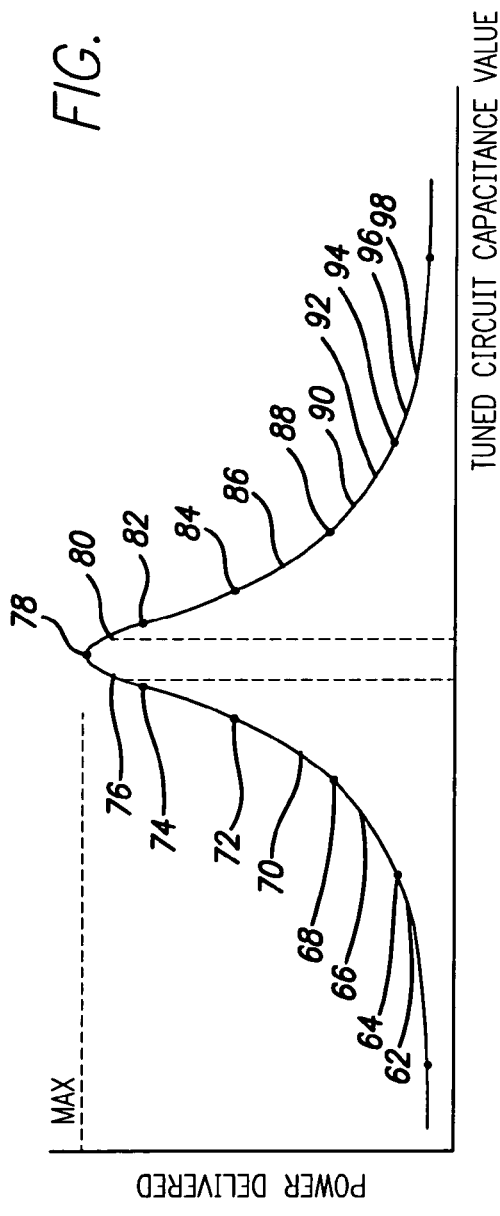
FIG. 16A is a graph depicting the power delivered to the tuned circuit versus the tuned circuit capacitance value for the embodiment of FIG. 15.
Figure 16B:
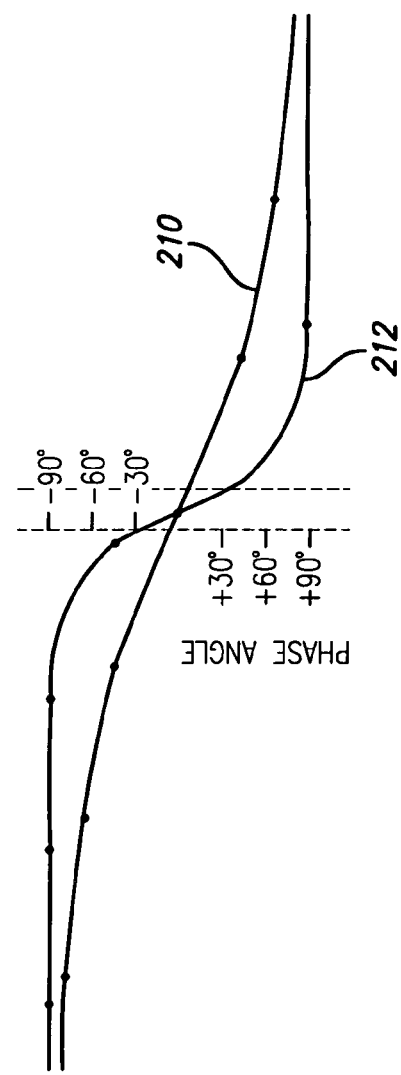
FIG. 16B is a graph of the phase angle difference between the reference oscillator signal and the inductor current as a function of tuned circuit capacitance value for the embodiment of FIG. 15.

A still further embodiment of the present invention is show in FIG. 15 which relies on the principles of a phase locked loop to maintain the resonant frequency of the tuned circuit 16 equal to the reference frequency. To that end, the phase (angle) of the current flowing through inductor L is compared to the phase (angle) of the reference frequency signal generated by oscillator 28 and any phase difference detected is processed by microcontroller 26 to adjust the capacitance value of the tuned circuit 16 until the phase difference detected is within a prescribed value. More specifically, sense resistor 194 is coupled between inductor terminal 131 and ground. The differential inputs 198 and 200 of differential amplifier 202 are coupled across sense resistor 194 such that the phase of the voltage appearing across resistor 194 as a result of the phase of the current (current phase signal) flowing through the resistor 194 can be detected. The output 204 of amplifier 202 is supplied to one input of a phase comparator 206 and the signal appearing at the input 19 of amplifier 18 (voltage phase signal) is supplied to the second input of comparator 206. The comparator 206 may be any one of a number of conventional phase comparators known in the art capable of providing an output signal 208 in proportion to the difference of the phase of the signals appearing at output 204 and input 19. The comparator output signal 208 is applied to microcontroller 26 for processing in a manner consistent with the processing of the current sense signal of the embodiments of FIGS. 1, 11 and 14. More specifically, and with reference to FIG. 16A (showing only one maximum power point), as the microcontroller 26 commands the relay controller 30 to advance from switch position 60 to switch position 98 and beyond, the phase of the signal appearing at output 204 will vary from about −90 degrees through zero degrees at resonance to about +90 degrees as the capacitance of the capacitor bank 15 is sequentially increased in accordance with the method shown in FIG. 17. The invention described herein serves to maintain the phase of the current signal and the phase of the voltage signal to be equal or within a prescribed range of values. For high Q tuned circuits, the signal phase change at or near resonance will be more rapid than for low Q tuned circuits. For example and with reference to FIGS. 16A and 16B, two phase response curves 210 and 212, are shown with the Q relating to curve 210 being smaller than the Q relating to curve 212. Accordingly, the prescribed range of values is selected based upon the Q of the tuned circuit. Although not to be used in a limiting sense, a preferred range of prescribed values for the difference of the phase of the current signal and the phase of the voltage signal is ±30 degrees (relating to points 80 and 76 respectively, on the power delivered curve shown in FIG. 16A). Moreover, although the foregoing discussion was devoted to using the phase of the inductor current as one parameter, it is within the contemplation of the present invention to use other parameters such as the voltage across the inductor that is capacitively coupled to the comparator 206 as a parameter to compare with the reference oscillator signal in terms of a phase differential between such signals.

Figure 17:
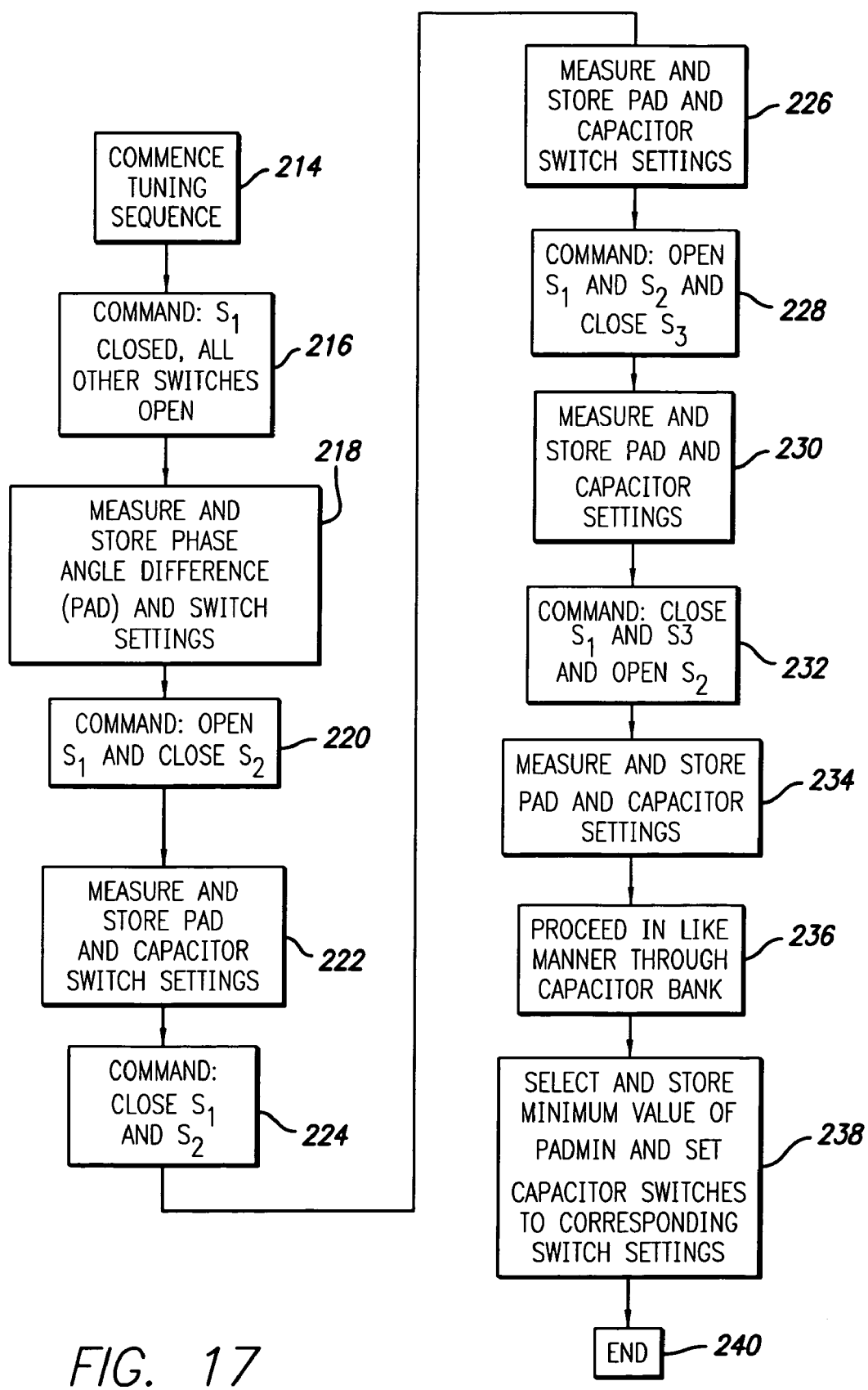
FIG. 17 is a flow chart of automatic tuning protocol of the embodiment of FIG. 15 to establish the capacitor switch settings to obtain maximum power delivery to the tuned circuit.

The initial tuning sequence is shown in FIG. 17, which mirrors the sequence of steps shown in FIG. 2 except that measurement of the (phase) difference between the phase of the current flowing in inductor coil 14 and the phase of the reference frequency signal appearing at input 19 is used as a control function, rather than the current delivered by the power amplifier 18. In all other respects, the methods disclosed in FIGS. 2 and 17 closely track one another. Moreover, with regard to the re-tuning sequence as shown in the flow chart of FIG. 4, the decision made in the instant case as to whether successful re-tuning has occurred, is based upon whether the phase difference is within a preselected range of acceptable values. For example, if the phase difference is within ±30 degrees of the initially tuned condition, then successful re-tuning is considered to have been accomplished. Referring to FIG. 17, the initial tuning sequence commences at block 214 and all switches except S1 are closed in block 216. In block 218 the phase difference between the phase of the current flowing in inductor coil 14 and the phase of the reference frequency signal appearing at input 19 is determined and its value stored in conjunction with the present capacitor switch setting. Proceeding from blocks 220 through block 236, the capacitor switches are sequentially opened and closed in the same manner as discussed for the embodiment illustrated in FIG. 2 with phase difference values stored in conjunction with capacitor switch settings rather than power amplifier current values. In block 238, the minimum value of the phase angle difference is determined and the capacitor switches are set corresponding to such minimum phase angle difference.

Figure 18:
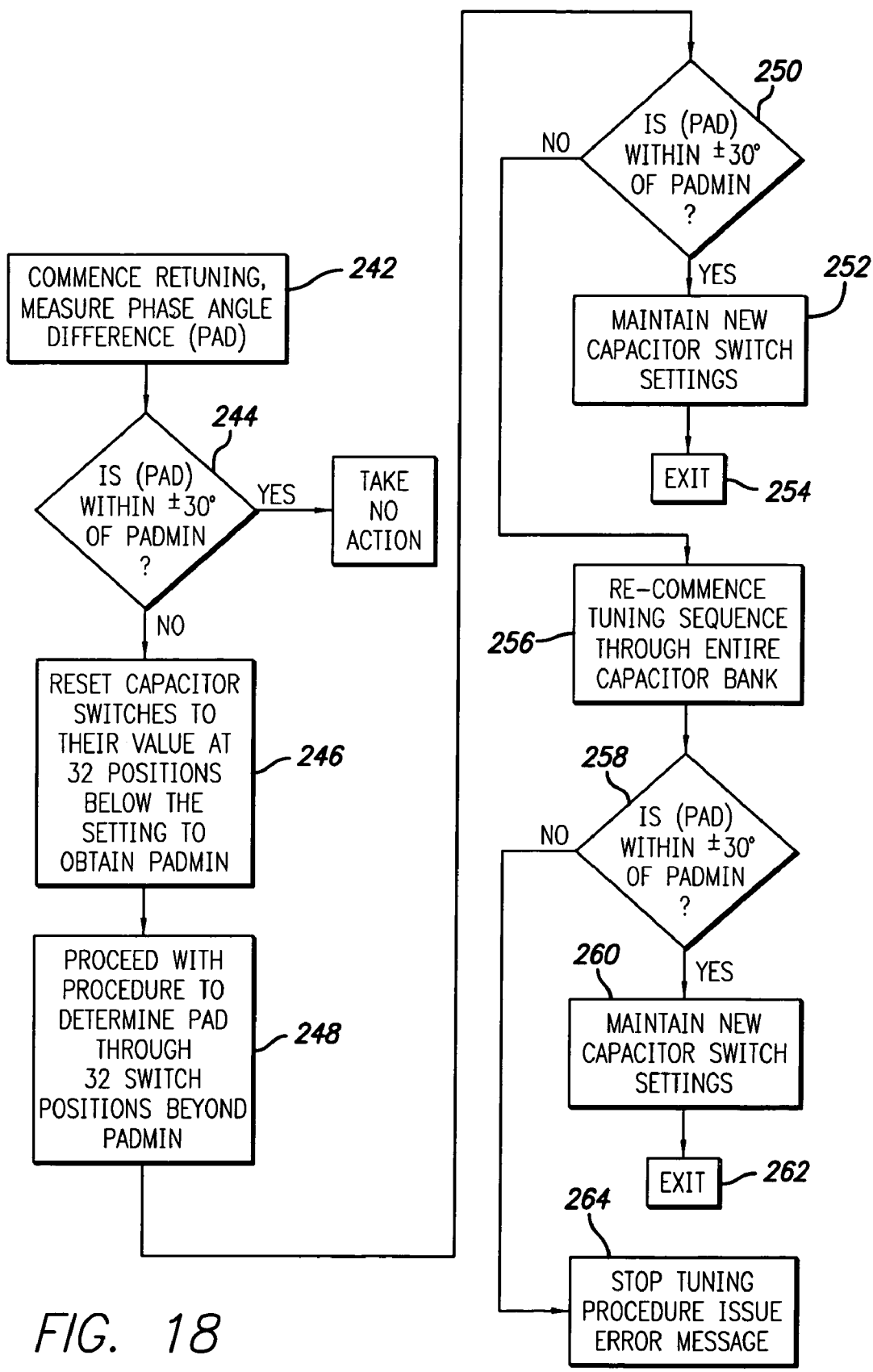
FIG. 18 is a flow chart of the embodiment of FIG. 15 to determine a capacitor switch setting to reestablish maximum power delivery to the tuned circuit.

With reference to FIG. 18 the re-tuning procedure commences at block 242 where the phase angle difference (PAD) is obtained at the comparator output 208. A check is made in block 244 as to whether the obtained PAD is within a predetermined range of values relative to the PADMIN determined at block 238. If the PAD is within the acceptable range then no action is taken and the capacitor switches are maintained unchanged. If however, the PAD is outside the acceptable range, then in block 246 as an initial re-tuning starting point, the capacitor switches are set to a number of settings away from that which provided the PADMIN. In the embodiment of FIG. 18, the number of settings is selected to be 32. The acceptable range for the PAD may be selected to be from about ±5 to ±60 degrees and in the embodiment of FIG. 18, it is selected to be ±30 degrees. The PAD may be in terms of lag or lead such that the range is understood to be ±30 degrees. An alternate predetermined range of values may be in terms of a percentage of the PADMIN so for example, if the PAD is outside a fixed percentage of the PADMIN, then the re-tuning sequence is initiated at block 246. Moreover, since the direction of the error is known, the microprocessor may be programmed to determine in which direction (shown as below in FIG. 18) to set the number of settings away from that which provided the PADMIN.

The procedure described in FIG. 18 continues through the 64 switch settings and in block 250 the PAD is continually evaluated for each of such 64 switch settings set in block 248, to determine whether it is within the preselected range of acceptable values (±30 degrees of PADMIN). If so, then at block 252 the switch settings are selected that provide the acceptable PAD. If not, then at block 258, the re-tuning sequence is performed through the entire capacitor bank. At block 258, the PAD is continually evaluated to determine whether it is within the preselected range of acceptable values (±30 degrees of PADMIN). If so, then at block 260, the switch settings are selected that provide the acceptable PAD. If not, then at block 264, the re-tuning sequence is terminated and an error message is issued advising of the failure to successfully re-tune.

Although the phase-locked loop (PLL) embodiment of FIG. 15 has been described in terms of a switchable capacitor bank, it is to be understood that the motor driven variable capacitor embodiment of the present invention shown in FIG.

11 is also contemplated by the present invention. Accordingly, the tuning sequence as shown in FIG. 12 is applicable to describe the PLL embodiment utilizing the motor driven variable capacitor except that the PAD and the PADMIN, are used in place of the PA CURRENT/POWER VALUES and MAX POWER POINT, respectively. Similarly, the re-tuning sequence of FIG. 13 is applicable as well, with the parameter replacements defined immediately above and the tests performed in blocks 174, 184 and 200 to comprise whether the PAD is within ±30 degrees of PADMIN. Additionally, prior to completing an initial tuning or re-tuning sequence, a check may be made as to whether the coil current is sufficient to generate a magnetic field sufficient to reliably communicate with the implanted microdevice. This test is not shown in the flow charts and the value of a threshold amount of coil current is typically determined empirically.

Figure 19:
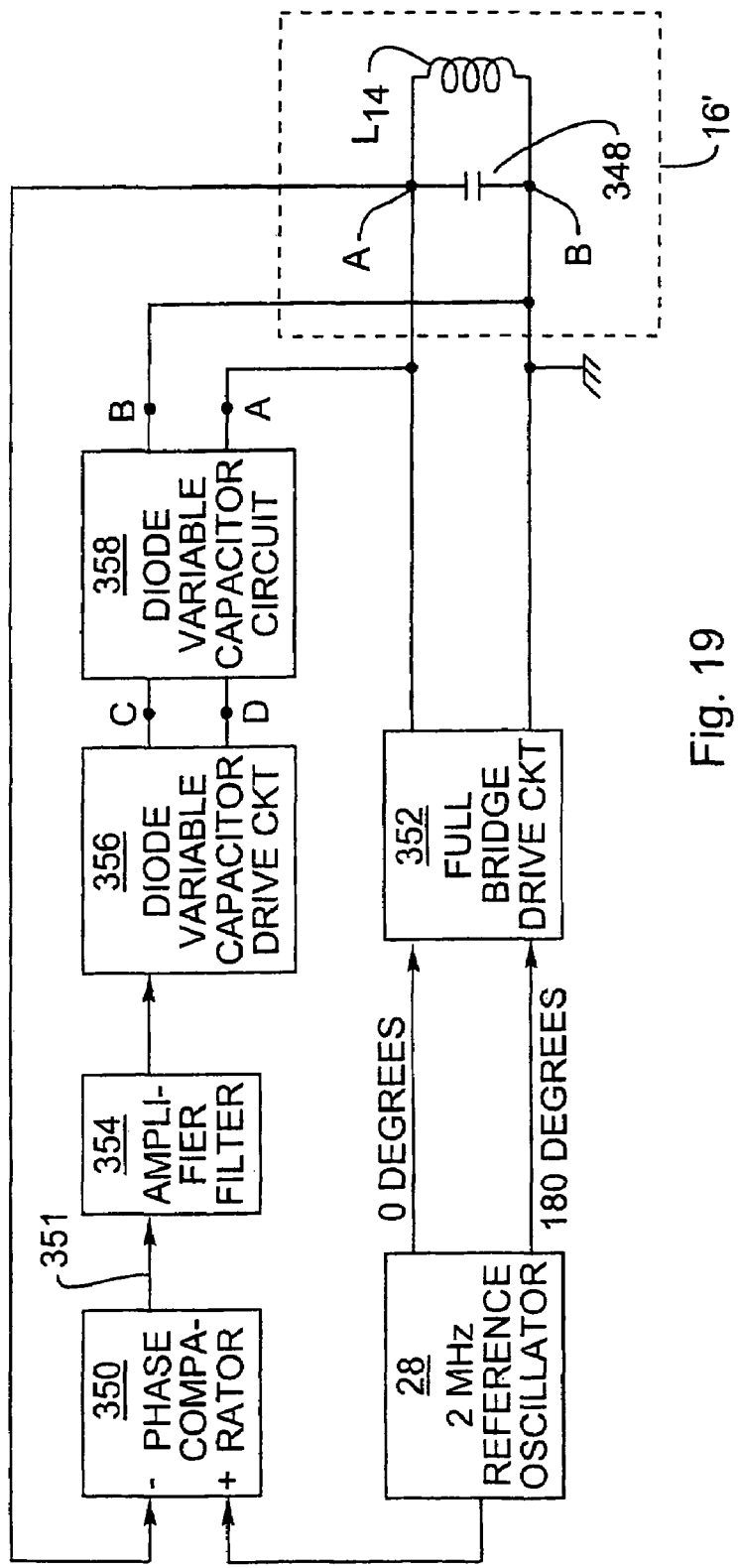
FIG. 19. Is a block diagram of an alternate embodiment of a tuning system utilizing a diode variable capacitor.

A still further alternative for the variable capacitor is the use of a diode variable capacitor arranged in conjunction with the tuned circuit 16' for establishing its resonant frequency. A block diagram of a system utilizing a diode variable capacitor (varicap) as the controlled element to provide a variable capacitor positioned in parallel with inductor 14 is shown in FIG. 19. By varying the diode capacitance in a controlled manner, the capacitance of the tuned circuit 16' may be varied to a value that adjusts the resonant frequency of the tuned circuit to equal the 2 Mhz reference frequency.

More specifically and as is known in the art, a varicap device is characterized as being a diode having a terminal to terminal capacitance that can be varied as a function of the magnitude of the back bias voltage appearing across the diode terminals. At relatively low back bias voltage values, the varicap capacitance is relatively high and at relatively high back bias voltage values, the varicap capacitance is relatively low. Accordingly, by adjusting the back bias voltage across the diode, the capacitance appearing across the diode may be adjusted to a desired value. An embodiment utilizing the above concept for adjusting the overall capacitance value of tuned circuit 16' utilizing varicaps is shown in the diode variable capacitor circuit of FIG. 20. Although shown in a six diode parallel array arrangement, it is to be understood that a preselected number of diodes from at least one to greater than six is contemplated by the present embodiment of the invention. Each diode in the array is in series circuit arrangement with two blocking capacitors such as, for example, in the case of D1 where such diode is in series with capacitors 310 and 312. The contribution of the capacitance provided by D1 and C310 and C312 may be calculated using the known relationship for capacitors connected in series while also knowing the voltage of across the diode provided at terminals C-D (see FIG. 20). For the present case, and assuming the use of identical diodes, the capacitance value appearing at terminals A-B of the array would be six times the capacitance value of one leg (D1, C310 and C312) since the legs forming the array are connected in parallel circuit arrangement. The diodes D1 through D6 are connected to a voltage source at terminals C-D (see FIGS. 19 and 20) through respective resistors 324 to 346 each having a relatively high value of resistance. Accordingly, the relatively high resistance value of resistors 324 through 346 provides electrical connection to the diodes from the controlled voltage at terminals C-D while limiting any current flow through the back biased diodes D1 through D6. Moreover, capacitors C300 to C322 block the control voltage appearing at terminals C-D from appearing across inductor 14.

Considering a desired resonant frequency of 2 Mhz for tuned circuit 16' with an inductance value of 13 microhenrys (μH) for inductor 14, a tuned circuit capacitance value of about 487 picofarads (pf) is required. Tuned circuit fixed capacitor 348 has a value of about 400 pf. Accordingly, an additional capacitance of 87 pf is required to be added to the fixed capacitor to achieve a tuned circuit resonant frequency of 2 Mhz.

Figure 20:
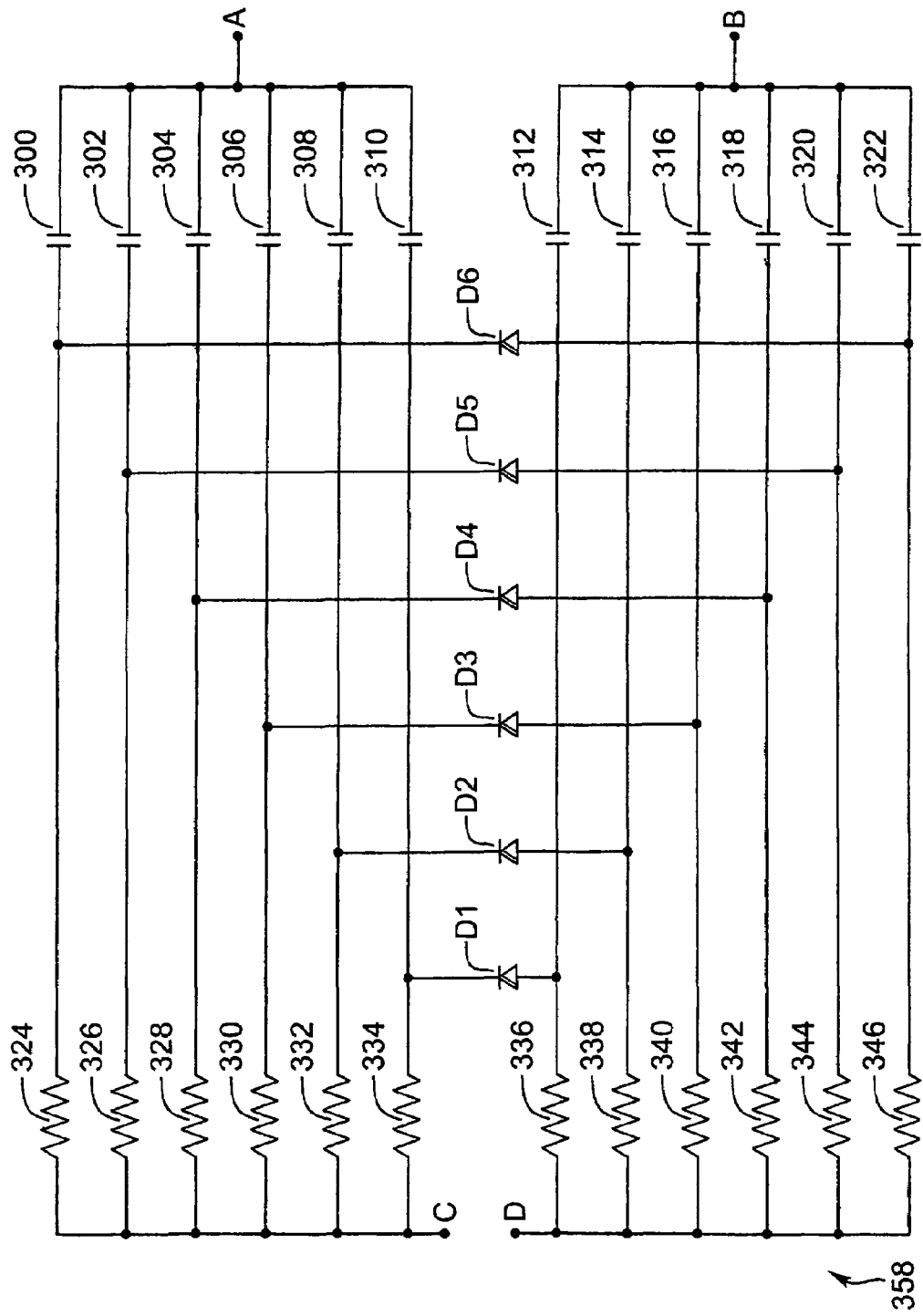
FIG. 20 is a circuit diagram of an embodiment of a diode variable capacitor circuit.

Ideally, the varicap circuit would provide, at its midrange of controllable capacitance values, a capacitance of about 87 pf. Table 1 shows a tabulation of the voltage applied across the varicap versus corresponding varicap capacitance values. As observed, the midpoint of the available capacitance values is 86 pf at a control voltage of 100 volts DC. As further observed, a change of about 57 pf or about 12% of the nominal required tuned circuit capacitance value, is available through a controlled voltage range of from 0 to 400 volts DC. While not departing from the spirit of the invention, it is to be understood that a greater or smaller range of capacitances values provided by the array of FIG. 20 is available by adding or removing diode legs, as required. Alternately, utilizing varicap devices having different voltage-capacitance ranges may also be used.

Referring to FIG. 19, operation of the present embodiment is as follows. The 2 Mhz reference oscillator 28 provides a 2 Mhz zero phase signal to the non-inverting input of phase comparator 350 as well as a zero phase and a 180° phase 2 Mhz signal to full bridge drive circuit 352. The full bridge drive circuit 352 provides a tuned circuit drive signal across terminals A-B of tuned circuit 16'. The inductor voltage at terminal A is provided to the inverting input of phase comparator 350. Any difference in phase between the reference oscillator signal and the inductor voltage which forms an error signal 351, is amplified and filtered by way of a low pass filter amplifier 354. The output of amplifier 354 is provided to varicap drive circuit 356 having a DC output voltage as a function of the phase comparator output signal (error signal) 351. Nominally the varicap drive circuit is configured to provide an output that is about 100 volts to provide a varicap capacitance of about 86 pf (see Table 1).

TABLE 1

| V BIAS D.C. | Capacitance pf |
|---|---|
| 0 | 130 |
| 20 | 108 |
| 50 | 96 |
| 75 | 91 |
| 100 | 86 |
| 150 | 80 |
| 200 | 77 |
| 300 | 74 |
| 400 | 73 |

Under such conditions the tuned circuit 16' will have a resonant frequency of 2 Mhz in phase with the reference signal generated in reference oscillator 28.

If the drive circuit 352 is configured such that the phase of the inductor voltage is normally 180° out of phase with the reference oscillator signal, then selection of inverting and non-inverting inputs of phase comparator 350 may be selected to achieve minimizing the error signal 351 when the resonant frequency of the turned circuit 16' equals to the reference frequency. At such time that the inductance value of inductor 14 changes due to influences previously described, the resonant frequency of the tuned circuit 16' will correspondingly change causing a phase shift of the inductor voltage which when measured against the phase of the reference oscillator signal in phase comparator 350 causes a corresponding change in error signal 351. The change in error signal 351 causes a corresponding change of the output of diode variable capacitor drive circuit 356 which in turn causes an offsetting change in varicap capacitance (diode variable capacitor circuit 358) to return the resonant frequency of tuned circuit 16' back to 2 Mhz. A decrease in the inductance value of inductor 14 will require an increase in varicap capacitance and vise versa to maintain a nominal resonant frequency. With the present selection of component values, the varicap circuit can compensate inductance value change for inductor 14 inductance value changes from about 11.9 pH to about 13.4 pH. It is well within the contemplation of this embodiment to provide the varicap circuit with greater ranges of available capacitance values to accommodate greater value of inductance changes and vise versa.

Figure 21:
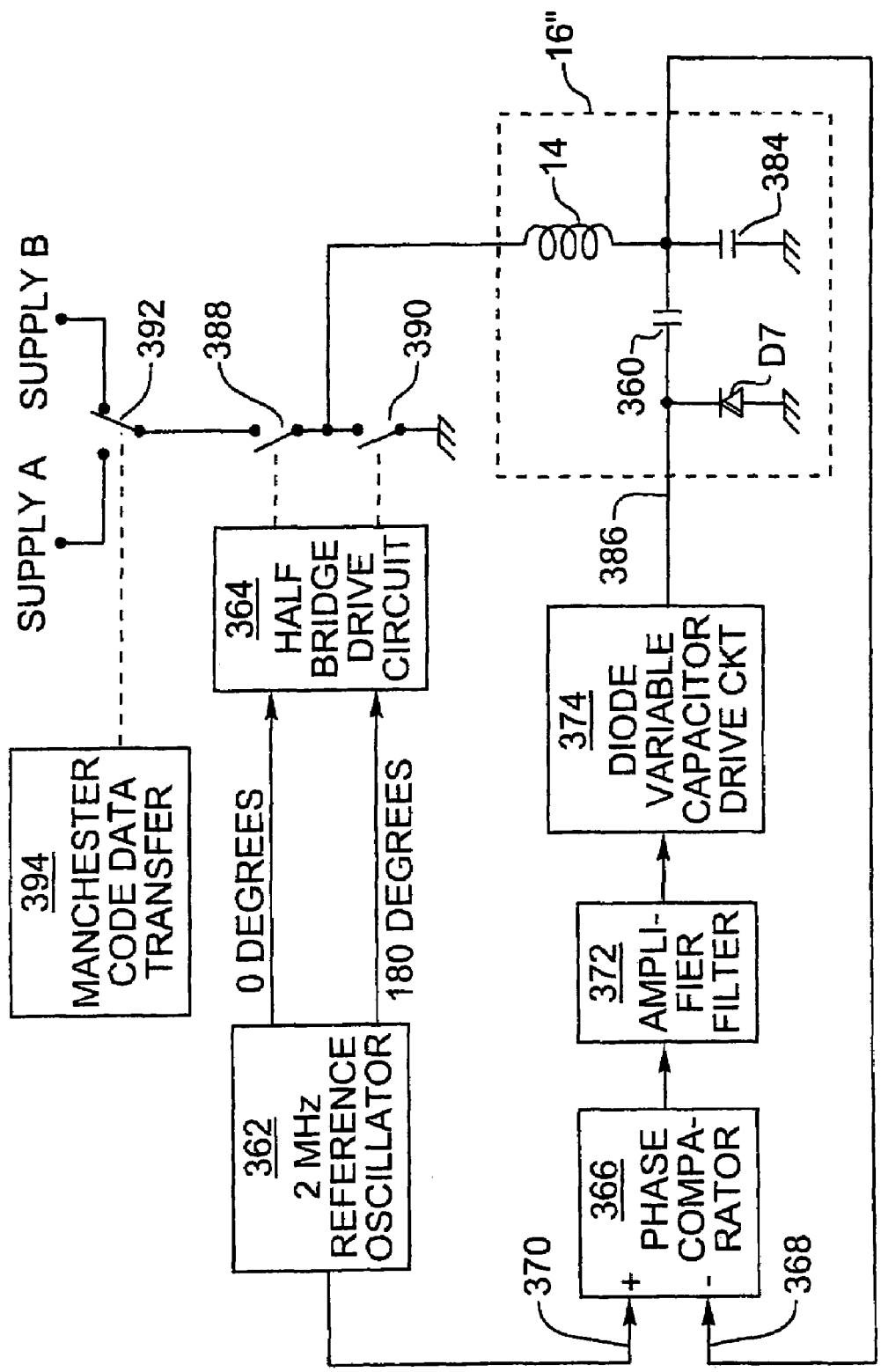
FIG. 21 is an alternate embodiment of the tuning system of FIG. 19.

An alternate embodiment of the present invention shown in FIG. 19 utilizing a series circuit arrangement of the tuning capacitor 384 and inductor 14 is shown in FIG. 21. The diode D7 which functions as the varicap, is in series circuit arrangement with isolation capacitor 360. A function of capacitor 360 is to isolate the inductor 14 and capacitor 384 from the DC output voltage output of drive circuit 374. The series combination of D7 and C360 is in parallel circuit arrangement with tuned circuit capacitor 384. Such arrangement provides the overall tuned circuit capacitance which is in series circuit arrangement with inductor 14 and establishes the resonant frequency of the tuned circuit 16". In a manner similar to that previously discussed regarding the embodiment of FIGS. 19 and 20, a controllable DC voltages is applied across D7, to adjust the effective capacitance of D7, which ultimately adjusts the resonant frequency of the tuned circuit 16". More specifically, and with reference to FIG. 21, a reference signal generator 362 provides a reference signal (for the present case but not limiting case, to 2 Mhz) to drive circuit 364. Circuit 364 is a one-half bridge drive circuit that drives turned circuit 16" at the 2 Mhz reference frequency. The voltage appearing across the tuned circuit capacitor 384 is applied to one input (368) of phase comparator 366 with the 2 Mhz reference frequency being applied to the other phase comparator input (370). Since the phase of the voltage across capacitor 384 lags the phase of the voltage appearing across the inductor 14 with respect to ground, the phase of the reference applied to input 370 is shifted by −90° to thereby calculate the appropriate error signal by the phase comparator 366.

When the tuned circuit 16" has a resonant frequency of 2 Mhz, the phase shifted reference signal and the voltage appearing across capacitor 384 will be in phase. Any phase error appearing at the output of phase comparator 366 is amplified by amplifier/filter 372 for driving varicap drive circuit 374. The amplifier/filter 372 serves to pass amplified low frequency signals to the diode variable capacitor circuit 374 and filter out and thus prevent any undesirable high frequency signals from reaching the diode variable capacitor circuit 374. Diode variable capacitor drive circuit 374 provides a DC voltage across diode D7 in a manner similar to that as previously described for the circuit shown in FIG. 20. The range of controllable DC voltage provided by circuit 374 is determined by the range of expected diode capacitance changes needed to compensate for the range of expected inductance value changes for inductor 14. Diode D7 (varicap) is selected to have a capacitance range adequate to compensate for the expected inductance changes of inductor 14. In the event that a single varicap is unable to contribute sufficient compensating capacitance, multiple varicaps may be used. Typically, the additional varicaps would be arranged in parallel circuit arrangement.

In operation, a positive DC voltage at the drive circuit output 386 causes a corresponding capacitance to be established across diode D7. The combination of such capacitance, with the blocking capacitor 360, is in parallel circuit relationship with tuned circuit capacitor 384, all of which contributes to the overall capacitance value of the tuned circuit 16". The reference oscillator 362 drives a one-half bridge circuit 364 which is coupled to a pair of switches 388 and 390. The drive circuit 364 causes switches 388 and 390 to alternately open and close at a 2 Mhz rate. The switch closures are timed so that switches 388 and 390 are never both closed at the same time. Closing the switches 388 and 390 at 2 Mhz, drives the tuned circuit 16" at 2 Mhz from power supply A or power supply B depending upon the position of switch 392. Switch 392 is driven by data transfer circuit 394 and as will be described below, digital data for information transfer to the microdevice by way of inductor 14, is accomplished by modulating the voltages driving inductor 14. This is accomplished by switching switch 392 at an informational transfer pattern consistent, for example, with a Manchester coding scheme. For a full discussion on such scheme, see U.S. Pat. No. 5,324,916 entitled "Implantable Microstimulator" to Schulman et al., which is incorporated herein by reference, in its entirety. Thus. by amplitude modulation of the 2 Mhz carrier frequency (reference frequency) control of information transfer from a remote controller to a microdevice may be accomplished. For a preferred data encoding scheme 16 cycles of the 2 Mhz carrier frequency may be chosen so as to provide one data bit of 8 micro-seconds in duration. The encoding scheme uses 16 cycles of the 2 Mhz carrier at its fully received amplitude (supply A) as a logical "0" and 8 cycles at the full amplitude (supply A) plus 8 cycles at the reduced amplitude (supply B) as a logical "1". The modulation depth which is a percentage determined by calculating the difference of the supply A and B voltages divided by the sum of the supply A and B voltages, is limited to allow power and carrier signals to be continuously available. For a modulation depth of about 17% the reduced amplitude supply B is about 0.7 times the values of the voltage of supply A. Manchester code data transfer circuit 394 then provides a control and information data flow mechanism concurrent with a tuned circuit turning and power delivery method.

It is recognized that the oscillatory voltages existing at the juncture of inductor 14 and capacitor 384 could be as high as 400 volts or even greater. Moreover, the DC voltage at the capacitor drive circuit output 386 may reach up to 500 volts to appropriately adjust the capacitance developed across diode D7. To avoid transferring such high voltages through interconnect cables and connectors between any control units, such as the DSP 12 and the inductor 14, the phase comparator 366, the amplifier filter 372, the diode variable capacitor drive circuit 374, the one-half bridge drive circuit 364, the switches 388, 390 and 392 and tuned circuit 16" may be all mounted on inductor 14. Such arrangement provides for compact and localized electronic "package" proximate to the inductor 14.

While the invention herein disclosed has been described by means of specific embodiments and applications thereof, numerous modifications and variations can be made thereto by one skilled in the art without departing from the spirit and scope of the invention. For example, although the microcontroller 26 is contemplated for the present invention for carrying out its defined monitor and control functions, it is to be understood that such monitor and control functions may also be undertaken by a state machine device. Accordingly, the devices may also be considered simply as a processor.

What is claimed is:

1. A tuning system for a magnetic field generator comprising:

a tuned circuit comprising a magnetic field generating inductor, a fixed capacitor and an adjustable capacitor, the inductance value of the inductor and the capacitance value of the capacitors establishing the resonant frequency of the tuned circuit;

a tuned circuit drive circuit having an output coupled to and adapted to drive the tuned circuit and deliver power thereto;

a reference frequency oscillator circuit providing a reference frequency signal, said oscillator circuit coupled to the tuned circuit drive circuit so as to cause said drive circuit to drive the tuned circuit at the reference frequency; and a sense circuit coupled to the reference frequency oscillator circuit and adapted to sense a first parameter related to the reference frequency signal, the sense circuit in electrical communication with the inductor and adapted to sense a second parameter related to the inductor and provide an error signal as a function of the first and second parameters, wherein the power delivered by the tuned circuit drive circuit to the tuned circuit is a function of the resonant frequency of the tuned circuit, and wherein the sense circuit monitors the error signal and causes the adjustable capacitor to be adjusted to a capacitance value that optimizes the error signal to thereby optimize the power delivered by the tuned circuit drive circuit, wherein the reference frequency signal is a voltage signal and the first parameter is the phase angle of such voltage signal and wherein the second parameter is the phase angle of the voltage across the inductor, wherein the sense circuit provides the error signal being the difference of the phase angle between the first and second parameters, each of the phase angles being measured relative to a pre-selected reference.

2. The tuning system of claim 1 wherein the sense circuit causes the adjustable capacitor to be adjusted so as to obtain a minimum value of the error signal, such minimum value being defined as the optimal value thereof.

3. The tuning system of claim 2 wherein the adjustable capacitor is a diode variable capacitor (varicap) arranged in parallel circuit relationship with the fixed capacitor, the capacitance value of said varicap being a function of the voltage across the varicap, the tuning system further comprising a varicap drive circuit coupled to said sense circuit and adapted to vary the voltage across the varicap, and thereby the capacitance thereof, as a function of the error signal, whereby the capacitance of the tuned circuit is thereby adjusted to cause the resonant frequency of the tuned circuit to equal the reference frequency.

4. The tuning system of claim 3 wherein the adjustable capacitor comprises a plurality of varicaps in parallel circuit arrangement.

5. The tuning system of claim 2 wherein the inductor is in series circuit relationship with the fixed capacitor and wherein the adjustable capacitor is a diode variable capacitor (varicap) arranged in parallel circuit relationship with the fixed capacitor, the capacitance value of said varicap being a function of the voltage across the varicap, the tuning system further comprising a varicap drive circuit coupled to said sense circuit and adapted to vary the voltage across the varicap, and thereby the capacitance thereof, as a function of the error signal, whereby the capacitance of the tuned circuit is thereby adjusted to cause the resonant frequency of the tuned circuit to equal the reference frequency.

6. The tuning system of claim 5 wherein the varicap drive circuit provides a direct current (DC) voltage across the varicap, said drive circuit further comprising an isolation capacitor disposed between the varicap and fixed capacitor to isolate the fixed capacitor from said DC voltage.

7. The tuning system of claim 6 wherein the inductor comprises a plurality of turns of a single conductor embedded within a nontoxic material, the adjustable capacitor, the fixed capacitor, the isolation capacitor and the varicap drive circuit being mounted on the inductor.

8. The tuning system of claim 7 further comprising at least two power sources adapted to provide power to the tuned circuit, wherein the drive circuit further comprises a modulation circuit adapted to transfer encoded information to the tuned circuit by alternately coupling the tuned circuit to selected ones of said at least two power sources.

9. The tuning system of claim 8 wherein the power sources have different magnitudes, and wherein the encoded information is defined by a train of information frames, each information frame having a predetermined number of data bits, each data bit having one of said different magnitudes and a corresponding duration, the data bits arranged within the information frame in a prescribed manner.

10. An automatic tuning system for a magnetic field generator comprising:

tuned circuit means comprising inductor means and capacitor means, the values of the inductor means and capacitor means establishing the resonant frequency of the tuned circuit means, tuned circuit drive means for delivering power to the tuned circuit means at a reference frequency; and means for adjusting the resonant frequency of the tuned circuit means for maximizing the power transferred from the power means to the tuned circuit means, whereby the power delivered by the power means is a function of the resonant frequency of the tuned circuit, wherein the adjusting means adjusts the value of the capacitor means for adjusting the resonant frequency of the tuned circuit means to equal the reference frequency; wherein the delivered power is maximized when the resonant frequency of the tuned circuit means equals the reference frequency, and monitoring means for monitoring the phase angle of the reference frequency and the phase angle of the voltage appearing across the inductor means and providing an error signal being the difference of the phase angle of the reference frequency and the phase angle of the voltage appearing across the inductor means wherein the adjusting means adjusts the resonant frequency of the tuned circuit means for obtaining an optimal value of the error signal, each of the phase angles being measured relative to a pre-selected reference, wherein the optimal value of the error signal is a minimal value thereof.

11. The system of claim 10 wherein the capacitor means is in parallel circuit relationship with the inductor means, wherein the capacitor means comprises a fixed capacitor and varicap means, said varicap means arranged in parallel circuit relationship with the fixed capacitor, the capacitance value of said varicap means being a function of the voltage across the varicap means, the tuning system further comprising a varicap drive circuit means coupled to said monitoring means and adapted to vary the voltage across the varicap means and thereby the capacitance thereof as a function of the error signal, whereby the capacitance of the tuned circuit means is adjusted so as to maintain the resonant frequency of the tuned circuit means at the reference frequency to thereby maintain the error signal at the optimal value.

12. The system of claim 10 wherein the capacitor means is in series circuit relationship with the inductor means, wherein the capacitor means comprises a fixed capacitor and varicap means, said varicap means arranged in parallel circuit relationship with the fixed capacitor, the capacitance value of said varicap means being a function of the voltage across the varicap means, the tuning system further comprising a varicap drive circuit means coupled to said monitoring means and adapted to vary the voltage across the varicap means and thereby the capacitance thereof as a function of the error signal, whereby the capacitance of the tuned circuit means is thereby adjusted to maintain the resonant frequency of the tuned circuit means at the reference frequency to thereby maintain the error signal at the optimal value.

13. The system of claim 12 wherein the varicap means includes an isolation capacitor to isolate the capacitor means from the varicap drive circuit.

14. In a tuning system for a magnetic field generator comprising, a tuned circuit comprising at least a magnetic field generating inductor having an inductance value and a diode variable capacitor (varicap) having a capacitance value being a function of a direct current (DC) voltage applied across the varicap, the tuned circuit resonant frequency being a function of the inductance value and capacitance value, a reference frequency signal generator, a phase comparator circuit adapted to provide an error signal as a function of the difference between the phase of the voltage across the inductor and the phase of the reference frequency, a varicap drive circuit adapted to provide a DC voltage across the varicap as a function of the error signal, a method of tuning the tuned circuit to have a resonant frequency equal to the reference frequency comprising the steps of:
  (1) measuring the error signal provided by the phase comparator circuit;
  (2) adjusting the voltage across the varicap as a function of the error signal; and
  (3) maintaining the voltage across the varicap at the value that provides the minimum value of the error signal.

15. An automatic tuning system for a magnetic field generator comprising:
  tuned circuit means comprising inductor means and capacitor means, the values of the inductor means and capacitor means establishing the resonant frequency of the tuned circuit means,
  tuned circuit drive means for delivering power to the tuned circuit means at a reference frequency;
  sense means for sensing a first phase angle relating to a signal associated with the inductor means and for sensing a second phase angle relating to a signal associated with the reference frequency, said sense means providing an error signal being the difference between the first and second phase angles; and
  microcontroller means for adaptively adjusting, as a function of the error signal, the resonant frequency of the tuned circuit means for maintaining maximum power transfer from the tuned circuit drive means to the tuned circuit means, whereby the power delivered by the tuned circuit drive means is a function of the resonant frequency of the tuned circuit, wherein the delivered power is maximized when the resonant frequency of the tuned circuit means equals the reference frequency.

* * * * *